US008470535B2

(12) United States Patent
McMaster et al.

(10) Patent No.: US 8,470,535 B2
(45) Date of Patent: Jun. 25, 2013

(54) TWO STAGE NUCLEIC ACID AMPLIFICATION USING AN AMPLIFICATION OLIGOMER

(75) Inventors: Gary McMaster, Ann Arbor, MI (US); Yunqing Ma, San Jose, CA (US)

(73) Assignee: Affymetrix, Inc., Santa Clara, CA (US)

( * ) Notice: Subject to any disclaimer, the term of this patent is extended or adjusted under 35 U.S.C. 154(b) by 0 days.

(21) Appl. No.: 13/066,727

(22) Filed: Apr. 21, 2011

(65) Prior Publication Data

US 2011/0256536 A1 Oct. 20, 2011

Related U.S. Application Data

(62) Division of application No. 11/983,216, filed on Nov. 6, 2007, now Pat. No. 7,615,351.

(60) Provisional application No. 60/872,199, filed on Dec. 1, 2006.

(51) Int. Cl.
*C12Q 1/68* (2006.01)

(52) U.S. Cl.
USPC .............. 435/6.11; 436/501; 536/23.1

(58) Field of Classification Search
None
See application file for complete search history.

(56) References Cited

U.S. PATENT DOCUMENTS

| 4,868,105 A | 9/1989 | Urdea et al. |
|---|---|---|
| 5,124,246 A | 6/1992 | Urdea et al. |
| 5,635,352 A * | 6/1997 | Urdea et al. ............ 435/6.18 |
| 5,681,697 A | 10/1997 | Urdea et al. |
| 5,849,481 A | 12/1998 | Urdea et al. |
| 5,981,180 A | 11/1999 | Chandler et al. |
| 7,927,798 B2 * | 4/2011 | Zheng et al. ............ 435/6.15 |
| 2002/0172950 A1 | 11/2002 | Kenny et al. |
| 2006/0286583 A1 | 12/2006 | Luo et al. |

FOREIGN PATENT DOCUMENTS

WO   WO 2007/001986   1/2007

OTHER PUBLICATIONS

Baner et al. (1998) "Signal amplification of padlock probes by rolling circle replication," *Nucleic Acids Res.*, 26(22):5073-5078.
Collins (1997) "A branched DNA signal amplification assay for qualification of nucleic acid targets below 100 molecules/ml." *Nucleic Acids Research*, 25(25): 2797-2984.
Flagella et al., Anal. Biochem. 2006, vol. 352, pp. 50-60.
Hatch et al. (1999) "Rolling circle amplification of DNA immobilized on solid surfaces and its application to multiplex mutation detection," *Genet Anal*, 15(2):35-40.
Kenny, D, Detection of Viral Infection and Gene Expression in Clinical Tissue Specimens Using Branched DNA (bDNA), Situ Hybridization (2002), 50(9): 1219-1227.

(Continued)

*Primary Examiner* — Stephanie K Mummert
(74) *Attorney, Agent, or Firm* — Quine Intellectual Property Law Group, P.C.

(57) ABSTRACT

This invention provides methods, compositions and systems to detect a nucleic acid of interest in a two-stage amplification. The two-stage amplification begins with a first non-enzymatic accumulation of an amplification oligomer that is the target substrate for a second nucleic acid amplification or assay. Two or more amplification oligomers can be used to allow multiplexed amplifications of two or more nucleic acids of interest with deconvolution based on unique detection signals or unique signal locations.

30 Claims, 11 Drawing Sheets

OTHER PUBLICATIONS

Masuda et al. (1999) "Analysis of chemical modification of RNA from formalin-fixed samples and optimization of molecular biology applications for such samples," *Nucleic Acids Res.*, 27(22):4436-4443.

Nallur et al. (2001) "Signal amplification by rolling circle amplification on DNA microarrays," *Nucleic Acids Res.*, 29(23):E118.

Notle (1998) "Branched DNA Signal Amplification for Direct Quantitation of Nucleic Acid Sequences in Clinical Specimens." *Avd. Clin. Chem.*, 33: 201-235.

Orum et al. (1999) *Clinical Chemistry*, 45(11): 1898-1905.

Player et al. (2001) "Single-copy Gene Detection sing Branched DNA (bDNA) in Situ Hybridization." *J. Histochem. and Cytochem.*, 49: 603-611.

Van Cleve et al. (1998) *Molecular and Cellular Probes*, 12(4): 243-247.

Zhang et al. (2005) *Journal of Biomolecular Screening*, 10(6): 549-556.

Zhang et al., Small Interfering RNA and Gene Expression Analysis Using aMultiplex Branched DNA Assay without RNA Purification, Journal of Biomolecular Screening (2005): 549-556.

\* cited by examiner

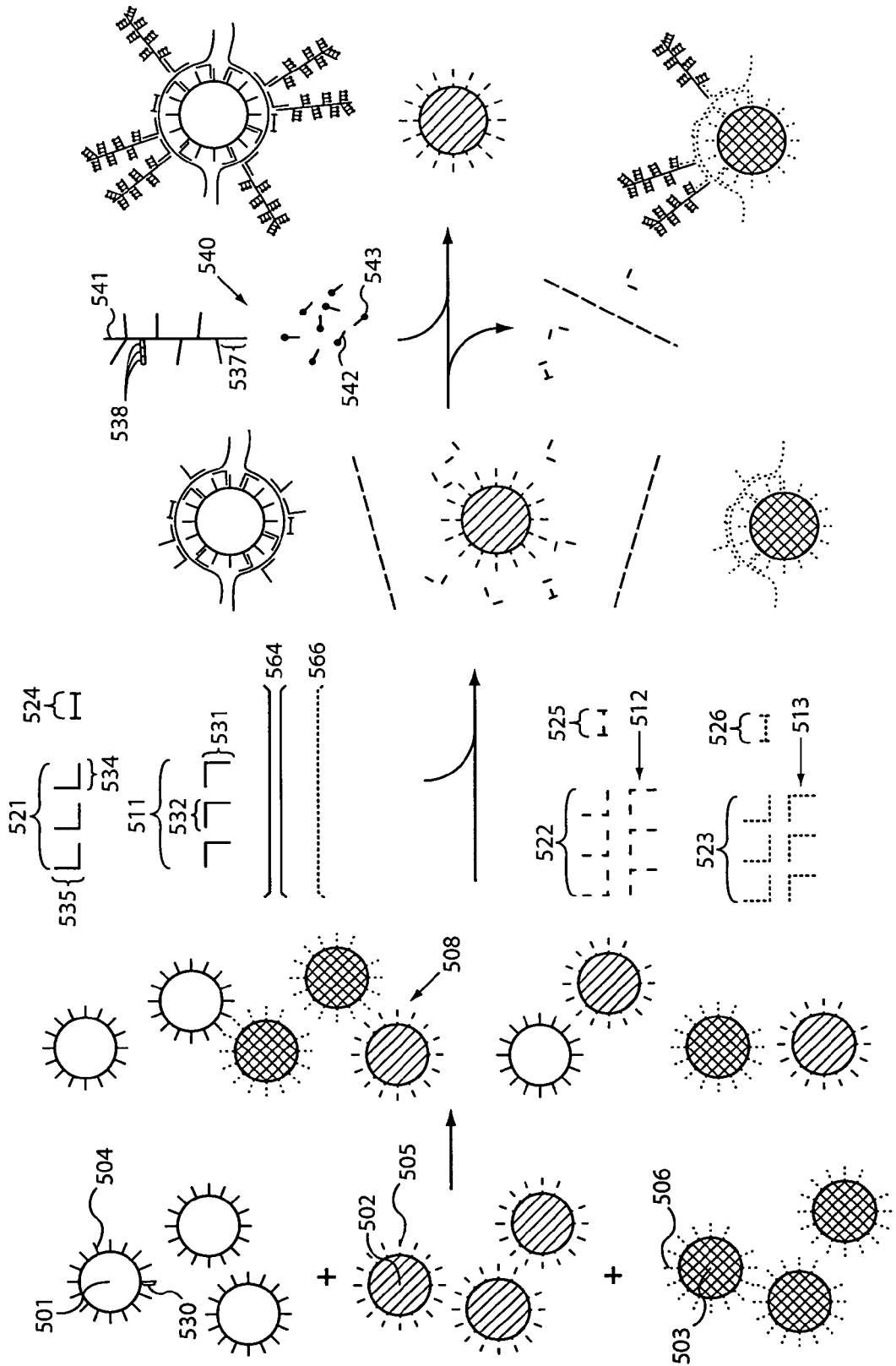

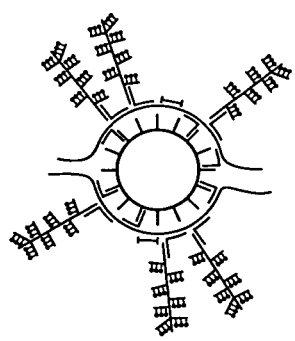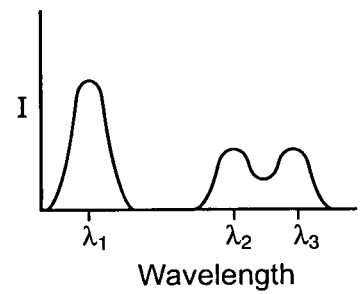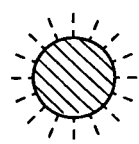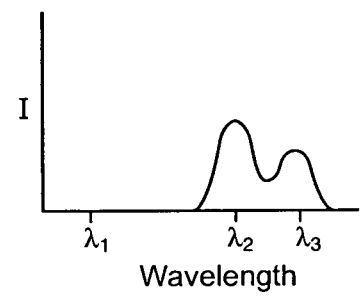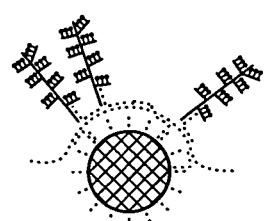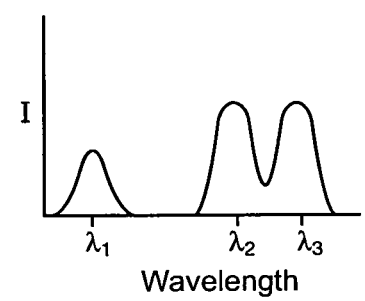
Fig. 6

TWO STAGE NUCLEIC ACID AMPLIFICATION USING AN AMPLIFICATION OLIGOMER

CROSS-REFERENCE TO RELATED APPLICATIONS

This application is a Divisional application claiming priority to and benefit of a prior to parent application Ser. No. 11/983,216, Two-Stage Nucleic Acid Amplification Using an Amplification Oligomer, by Gary McMaster, filed Nov. 6, 2007 now U.S. Pat. No. 7,615,351, which claims priority to and benefit of a prior U.S. Provisional Application No. 60/872,199, Two-Stage Nucleic Acid Amplification Using an Amplification Oligomer, by Gary McMaster, et al., filed Dec. 1, 2006. The full disclosure of the prior application is incorporated herein by reference.

FIELD OF THE INVENTION

The inventions are in the field of specific nucleic acid amplification and detection. The present methods and systems include a first target nucleic acid capture that provides, e.g., a first non-enzymatic amplification accumulating amplification oligomers that can become the target substrate for a second nucleic acid amplification or nucleic acid assay. Unique sequences in two or more different amplification oligomers can be used to direct them to be captured at separate locations or to capture reporter molecules with different signals, thus allowing analyses of two or more different nucleic acids at once from the same sample.

BACKGROUND OF THE INVENTION

A wide variety of techniques for amplifying nucleic acids are known in the art, including, but not limited to, PCR (polymerase chain reaction), rolling circle amplification, and transcription mediated amplification. (See, e.g., Hatch et al. (1999) "Rolling circle amplification of DNA immobilized on solid surfaces and its application to multiplex mutation detection" Genet Anal. 15:35-40; Baner et al. (1998) "Signal amplification of padlock probes by rolling circle replication" Nucleic Acids Res. 26:5073-8; and Nallur et al. (2001) "Signal amplification by rolling circle amplification on DNA microarrays" Nucleic Acids Res. 29:E118.) A labeled primer and/or labeled nucleotides are optionally incorporated during amplification. In many embodiments, the nucleic acids of interest are captured and amplified or detected but without an ability distinguish between two or more nucleic acids from the same sample. Further, the enzyme dependent amplification techniques often run inconsistently depending on the purity and complexity of the samples provided.

PCR amplifications are commonly used in nucleic acid analysis of samples, but suffer from limited amplicon size and difficulties providing conditions for consistent enzymatic activity. These problems are only heightened in analyses requiring reliable quantitation. For example, performance of quantitative PCR (QPCR) has faired poorly in quantitation of complex or degraded samples because it is generally limited to 75-85 by amplicon size, and multiple pooled gene-specific primers are required. QPCR requires a much greater nucleic acid purity than the bDNA assay and thus more steps to process the samples prior to analysis compared to the bDNA technology. A second problem that affects RNA quantification by QPCR is the required reverse transcription step to concert mRNA sequences of interest to cDNA. This enzymatic reaction is impeded by any base modifications, by secondary mRNA structure and by impurities in the RNA preparation. Although, introduction of a high temperature heating step during PCR amplification steps may partially reverse some of the RNA base modifications, for many samples these modifications are irreversible. Older samples are often so impaired that a decrease in average QPCR signal is >90%, requiring more input RNA and increasing Ct values to 35-40 (Masuda N, Ohnishi T, Kawamoto S, Monden M, Okubo K: Analysis of chemical modification of RNA from formalin-fixed samples and optimization of molecular biology applications for such samples, Nucleic Acids Res 1999, 27:4436-4443). With all these problems, QPCR has not been a satisfactory method of quantitating many types of nucleic acid samples. Furthermore these problems can not be cured by continued PCR amplification of the sample. Input of PCR products of a first amplification into a second full series of PCR amplifications only tends to further compound the amplification of errors originating in the first amplification.

One method of DNA amplification has the distinct advantage of not being dependent on enzymes to generate a signal. In a typical bDNA assay for gene expression analysis, a target mRNA whose expression is to be detected is released from cells and captured by a capture probe (CP) on a solid surface (e.g., a well of a microtiter plate) through synthetic oligonucleotide probes called capture extenders (CEs). Each capture extender has a first polynucleotide sequence that can hybridize to the target mRNA and a second polynucleotide sequence that can hybridize to the capture probe. Typically, two or more capture extenders are used. Probes of another type, called label extenders (LEs), hybridize to different sequences on the target mRNA and to sequences on an amplification multimer. Additionally, blocking probes (BPs), which hybridize to regions of the target mRNA not occupied by CEs or LEs, are often used to reduce non-specific target/probe binding. A probe set for a given mRNA thus consists of CEs, LEs, and optionally BPs for the target mRNA. The CEs, LEs, and BPs are complementary to nonoverlapping sequences in the target mRNA, and are typically, but not necessarily, contiguous. Signal amplification begins with the binding of the LEs to the target mRNA. An amplification multimer is then typically hybridized to the LEs. The amplification multimer has multiple copies of a sequence that is complementary to a label probe (it is worth noting that the amplification multimer is typically, but not necessarily, a branched-chain nucleic acid; for example, the amplification multimer can be a branched, forked, or comb-like nucleic acid or a linear nucleic acid). A label, for example, alkaline phosphatase, is covalently attached to each label probe. (Alternatively, the label can be non-covalently bound to the label probes.) In the final step, labeled complexes are detected, e.g., by the alkaline phosphatase-mediated degradation of a chemilumigenic substrate, e.g., dioxetane. Luminescence is reported as relative light unit (RLUs) on a microplate reader. The amount of chemiluminescence is proportional to the level of mRNA expressed from the target gene.

An exemplary embodiment of bDNA technology is schematically illustrated in FIG. 1, wherein a single target nucleic acid is captured and detected as an accumulation of label probes. A cell or tissue sample is lysed to produce a lysate including target nucleic acid 114. The target nucleic acid 114 (e.g., an mRNA whose expression is to be detected) is captured by capture probe 104 on solid support 101 (e.g., a well of a microtiter plate) through set 111 of synthetic oligonucleotide capture extenders. Each capture extender has a first polynucleotide sequence C-3 (152) that can hybridize to the target nucleic acid and second polynucleotide sequence C-1 (151) that can hybridize to the capture probe through sequence C-2 (150) in the capture probe. Typically, two or more capture extenders are used; optionally, one CE can be used to capture a target. Each label extender in label extenders set 121 hybridizes to a different sequence on the target nucleic acid, through sequence L-1 (154) that is complementary to the target nucleic acid, and to sequence M-1 (157) on amplification multimer (141), through sequence L-2 (155). Blocking probes (124), which hybridize to sequences in the target nucleic acid not bound by either capture extenders or label extenders, are often used in bDNA assays to reduce non-specific target probe binding. A probe set for a given target nucleic acid thus consists of capture extenders, label extenders, and optional blocking probes 124 for the target nucleic acid. The capture extenders, label extenders, and optional blocking probes are complementary to non-overlapping sequences in the target nucleic acid, and are typically, but not necessarily, contiguous. In this example, a single blocking probe is used; typically, an array of different blocking probes is used in an optimized bDNA assay.

Signal amplification can begin with the binding of the label extenders to the target nucleic acid. The amplification multimer is then hybridized to the label extenders. The amplification multimer has multiple copies of sequence M-2 (158) that is complementary to label probe 142. Label 143, for example, a fluorescent group, is covalently attached to each label probe. In the final step, labeled complexes are detected, e.g., by fluorometry. The amount of fluorescence can be proportional to the level of target nucleic acid originally present in the sample (a relationship describable, e.g., by a regression curve). However, the amplifications of a bDNA assay are limited, e.g., by the number of label probe sequence sites available on the amplification multimer and stearic hindrance in the amplification complex. When detecting two or more different target nucleic acids from the same sample, the typical bDNA assay provides only a combined result without separate identification or quantitation.

In view of the above, a need exists for methods of amplifying nucleic acids to a higher degree. It would be desirable to have systems that can highly amplify signals associated with the presence of a particular nucleic acid of interest in a sample without the use of amplifying enzymes. Benefits can be obtained from methods and systems capable of amplifying, quantitating and uniquely identifying signals from two or more different nucleic acid targets in the same assay. The present invention provides these and other features that will be apparent upon review of the following.

SUMMARY OF THE INVENTION

The present invention uses the unique characteristics of the two-stage amplification schemes described herein to provide powerful methods and systems to detect, quantify and/or identify one or more nucleic acids of interest in a sample. The methods include, e.g., a first bDNA amplification to provide a first amplification product, an amplification oligomer, that can act as a substrate for a second amplification or nucleic acid assay. The sequences of amplification oligomers can include encoded information useful in, e.g., associating the oligomer with the test target nucleic acid, directing a signal to a particular physical location, providing a substrate for an amplification enzyme, providing a target for a second bDNA amplification, and/or selecting a unique distinguishable reporter from an assay solution. The two-stage amplification schemes of the invention can drastically increase the sensitivity of a nucleic acid assay, identify the presence of a rare nucleic acid in a complex mixture of nucleic acids, determine the quantity of a rare or dilute nucleic acid in a sample, and/or allow quantitative and qualitative assays distinguishing two or more nucleic acids of interest from the same sample at once.

In a preferred embodiment of detecting a target nucleic acid of interest in a sample, each target is amplified to provide a number of amplification oligomers in a first non-enzymatic amplification, followed by a second amplification of the amplification oligomers to provide a still larger number of readily detectable labeled probes. For example, the method of detecting a nucleic acid of interest can include providing a sample comprising or suspected of comprising one or more nucleic acids of interest, capturing those nucleic acids of interest present in the sample on a first solid support, hybridizing a first amplification multimer directly or indirectly to the nucleic acid of interest, hybridizing the amplification multimer to one or more amplification oligomers, and detecting the previously hybridized amplification oligomers in a non-enzymatic nucleic acid assay. In a preferred embodiment, the non-enzymatic nucleic acid assay includes the steps of washing unbound components of the first amplification from the first solid support, melting the bound amplification oligomers from the first solid support and transferring them to a second solid support. The transferred amplification oligomers are then captured, e.g., by capture probes having sequences complementary to the amplification oligomers on the second solid support. Second amplification multimers are hybridized directly or indirectly to the complimentary sequences on the amplification oligomers (now acting as a target nucleic acid) and label probes are hybridized onto multiple complimentary sequences on the amplification multimer to provide abundant label signal. The presence of the target nucleic acid of interest in the original sample can be determined based on the amount of signal from label probe detected at the second solid support.

The amplification oligomers of the invention can have various sequences useful in directing them to bind at a solid support and useful in their amplification and detection. For example, amplification oligomers of the invention can include a nucleotide sequence complimentary to an amplification multimer M-2 sequence of a first amplification multimer, a nucleotide sequence complimentary to a capture extender C-3 sequence or to a capture probe C-2 sequence, and a nucleotide sequence complimentary to a label extender L-1 sequence or to an amplification multimer M-1 sequence of a second amplification multimer. In a preferred embodiment, the first amplification multimer is a component of a first bDNA assay, and the capture extender or the capture probe are components of a second bDNA assay. In preferred embodiments, the amplification oligomer nucleotide sequence complimentary to the amplification multimer M-2 sequence comprises from 20 to 80 nucleotides, or from 30 to 60 nucleotides, or about 50 nucleotides. In a preferred embodiment, the nucleotide sequence of the amplification oligomer complimentary to the capture extender C-3 sequence or to the capture probe C-2 sequence comprises from 20 to 60 nucleotides or about 50 nucleotides. In still more preferred embodiments, amplification oligomer nucleotide sequence complimentary to the label extender L-1 sequence or to the amplification multimer M-1 sequence of the second amplification multimer comprises from 20 to 40 nucleotides or about 28 nucleotides. In a typical embodiment, the amplification oligomer comprises a total length from 60 to 300 nucleotides, from 100 to 150 nucleotides, or about 130 nucleotides. In preferred embodiments, the amplification oligomers do not comprise a label.

The amplification oligomers can have complimentary sequences in the order: 1) the amplification multimer M-2 compliment; 2) the capture extender compliment or capture probe compliment; 3) label extender compliment or amplification M-1 compliment. In optional embodiments, the amplification oligomer does not include a compliment to a capture system. In an alternate preferred embodiment, the amplification oligomer nucleotide sequence complimentary to the amplification multimer M-2 sequence of a first amplification multimer is between 1) the nucleotide sequence complimentary to a capture extender C-3 sequence or to a capture probe C-2 sequence of a second amplification, and the nucleotide sequence complimentary to the label extender L-1 sequence or to an amplification multimer M-1 sequence of a second amplification multimer.

In preferred embodiments, particularly in matrixed amplification embodiments, the amplification oligomer has two or more sequences complimentary to a capture extender C-3 sequence or to a capture probe C-2 sequence, thus allowing cooperative hybridization in a second capture step. In a similar fashion, it is preferred that the amplification oligomer have two or more sequences complimentary to the label extender L-1 sequence or to the amplification multimer M-1 sequence of the second amplification multimer to allow the benefits of cooperative hybridization.

In the two-stage amplification methods, the target nucleic acid of interest (or amplification oligomer in a second non-enzymatic amplification) can be captured on a solid support directly, indirectly, covalently, by affinity, by hybridization, etc. For example, capturing can be through hybridization of a first capture probe on the solid support to a first capture extender and hybridization of the capture extender to a complimentary sequence on the nucleic acid of interest; through hybridization of the nucleic acid of interest directly to a capture probe; by affinity capture of the nucleic acid of interest (e.g., antibody capture of a hapten on an incorporated nucleotide analog); by capture of the nucleic acid of interest by the solid support substrate (e.g., by formation of a covalent bond in a chemical reaction or by molecular interactions, such as ionic, chelation or hydrophobic interactions).

The label probe system used to detect the presence of a nucleic acid of interest can be configured in a variety of ways. For example, the label probe system can include a covalently or non-covalently branched structure decorated with label probes and associated with the amplification oligomer in a second non-enzymatic amplification through a label extender. That is, the label system can include a label probe with a sequence complimentary to an amplification multimer, which has sequences complimentary to a label extender, which has sequences complimentary to the amplification oligomers. The label probe system can be configured to hybridize the amplification multimer directly to the amplification oligomer in the second amplification, e.g., an amplification multimer with sequences directly complimentary to the amplification oligomer, and to multiple label probes. Optionally, the a label probe system can include a system wherein the amplification oligomer consists of preamplifiers and amplifier nucleic acid strands, e.g., a preamplifier with a sequence complimentary to the amplification oligomer (optionally, indirectly through a label extender) and to an amplifier with a sequence comprising multiple sequence sites complimentary to label probes.

Noise can be reduced in the amplifications and sensitivity increased by reducing non-specific binding and careful control of hybridization stringency. In preferred embodiments, the label extender and capture extender are present in excess over complimentary first amplification multimer sequences in the second amplification. Blocking oligomers complimentary to the amplification oligomer can be provided in the first and/or second amplification reactions to reduce hybridization of amplification oligomers to first amplification multimers. In many embodiments, blocking probes complimentary to target nucleic acid strands not complimentary to intended label systems or capture systems are provided to reduce non-specific binding of undesired sample or system nucleic acids.

The nucleic acid of interest captured in the non-enzymatic amplifications of the invention can be nucleic acids from clinical specimens, research samples, forensic samples, and the like. The nucleic acids can be any type, such as e.g., DNA, cDNA, RNA, mRNA, rRNA, miRNA, siRNA and/or the like. In many embodiments, the target nucleic acid of interest is the amplification product of the first amplification, e.g., an amplification oligomer. The product of a first amplification can be detected in a nucleic acid assay, such as, e.g., a bDNA assay, PCR, LCR, a northern blot, a Southern blot, electrophoresis, and light absorbance. A positive result in the assay can be correlated to the presence of a nucleic acid of interest in the test sample.

Ultimate detection of a signal from the second amplification can be by any appropriate detection technique. For example, detection of the second amplification product can be by a bDNA assay, a northern blot, a Southern blot, electrophoresis, and light absorbance. In many embodiments, labeled product results from the second amplification, allowing ready detection of the product, e.g., by fluorometry, spectrophotometry, phosphorimaging, etc. For example, where the second amplification is a bDNA assay, a large amount of label probes, e.g., with fluorescent labels, can be present on amplification multimers at a solid support associated with a positive result for the presence of a nucleic acid of interest. In another example, wherein the second amplification is a PCR assay, the replicated nucleic acid can incorporate labeled nucleotides or be detectable using FRET (e.g., Taqman) probes.

Methods of the invention further provide a variety of ways to multiplex two or more nucleic acids of interest through the two-stage amplifications so that their presence can each be separately detected. The presence or absence of two or more nucleic acids of interest can be determined, e.g., by providing a sample comprising or suspected of comprising one or more nucleic acids of interest, capturing those nucleic acids of interest present in the sample on a first solid support, providing a first amplification multimer comprising a first M-1 sequence and capable of hybridizing directly or indirectly to a first nucleic acid of interest, providing a second amplification multimer comprising a second M-1 sequence different from the first M-1 sequence and capable of hybridizing directly or indirectly to a second nucleic acid of interest different from the first nucleic acid of interest; providing a first amplification oligomer comprising a sequence complimentary to the first amplification multimer and a second amplification oligomer comprising a sequence complimentary to the second amplification multimer, directly or indirectly hybridizing the captured nucleic acids of interest to the first or second amplification multimers, hybridizing the amplification oligomers to the hybridized amplification multimers, and detecting the previously hybridized amplification oligomers in a nucleic acid assay. Depending on the nature of the nucleic acid assay, the presence and/or quantity of each nucleic acid of interest can be determined from the same sample.

Different amplification oligomers accumulated on the same first solid support in a matrixed assay can be washed to remove residual components of the first amplification and then melted in a melting solution for transfer to one or more separate solid supports for one or more additional amplifications. For example, the amplification oligomers can be captured on a second solid support by, e.g., hybridizing a capture probe on the second solid support to a capture extender and hybridizing the capture extender to a complimentary sequence on the amplification oligomer; hybridizing the amplification oligomer directly to a capture probe on the second solid support; affinity capture of the amplification oligomer, and/or capture of the amplification oligomer through chemical interactions with the solid support substrate. The amplification oligomers captured on a second solid support can be detected, e.g., hybridizing the amplification oligomers to a preamplifier, hybridizing the preamplifier to an amplifier, hybridizing a label probe to the amplifier, and detecting a signal associated with the label probe. The detections of two or more different amplification oligomers can take place at the same locations on the additional solid support or at different locations. For example, the first amplification oligomers can be captured on a first of the additional solid supports and the second amplification oligomers can bee captured on a second of the additional solid supports, so that the presence of the first nucleic acid of interest can be detected as a signal emanating from the first solid support or the presence of the second nucleic acid of interest can be detected as a signal emanating from the second solid support.

In preferred embodiments of matrixed amplifications, the nucleic acid assay after the first amplification can be a second amplification, e.g., a second non-enzymatic amplification. For example, a first amplification oligomer product of the first amplification can have a sequence complimentary to a capture extender or capture probe on a second solid support, and a different second amplification oligomer product of the first amplification can have a sequence complimentary to a different capture extender or capture probe on the second solid support. The locations of the different capture probes on the solid support can be separated or common. For example, the capture extender or capture probe complimentary to the first amplification oligomer can be bound to the second solid support at one location and the other capture extender or capture probe complimentary to the second amplification oligomer can be bound to the second solid support at a different location. Optionally, the first and second amplification oligomers can be captured at entirely different solid supports (e.g., different beads). In such a case, detecting second amplification products can include contacting the amplification oligomers in a solution to second and third solid supports at the same time or contacting them in sequence.

The present invention includes systems to practice the methods of the invention. The systems can include hardware to carry out the transfers and provide conditions necessary to practice methods of the invention. The systems can include, e.g., computers, compositions of the invention, controlled heating plates, any of various solid supports, particle sorters, detector systems, fluid handling systems, and/or the like.

In the amplification systems, a nucleic acid of interest in a first bDNA amplification can be detected as the presence of an amplification oligomer in a second amplification. For example, a two-stage amplification system to detect a nucleic acid of interest can include 1) a first a bDNA amplification system wherein the nucleic acid of interest is the target nucleic acid, an amplification multimer with a plurality of sequences complementary to an amplification oligomer sequence; and, a non-enzymatic nucleic acid assay capable of detecting the amplification oligomer sequence. Detection of the amplification oligomer by the nucleic acid assay in such a system indicates the presence of the nucleic acid of interest in the bDNA amplification. In preferred systems, the amplification oligomer does not comprise a label. In preferred systems, the nucleic acid assay after the first amplification is a bDNA assay in which the amplification oligomer functions as a target nucleic acid. In alternate embodiments, the nucleic acid assay can be any nucleic acid assay, e.g., a northern blot, a Southern blot, electrophoresis, light absorbance, and/or the like.

In preferred embodiments of the systems, the amplification oligomer is a nucleic acid with sequences complimentary to multiple replicate sequences of an amplification multimer in a first amplification, and with sequences complimentary to capture a label system in a second amplification. For example, the amplification oligomer can include a sequence complimentary to an M-2 sequence of a first amplification multimer (functioning in a first amplification), to an L-1 sequence of a label extender or to an M-1 sequence of a second amplification multimer, and (optionally) to a C-3 sequence of a capture extender or to a C-2 sequence of a capture probe of a second amplification capture system.

First and/or second amplifications can take place on the surface of a solid support in systems of the invention. The solid supports can be in the form of surfaces, beads, particles, microspheres, conduit surfaces, chamber walls, multi-well plates, etc. The solid supports can be formed from, glass, silicon, silica, quartz, plastic, polystyrene, nylon, a metal, a ceramic, nitrocellulose, and/or the like. For example, bDNA amplifications or nucleic acid assays can take place on solid supports, such as, e.g., a bead (e.g., microsphere), a bead comprising a fluorescent dye, a paramagnetic bead, a multi-well plate, a membrane, and/or the like.

The systems of the invention can function in the multiplexing and deconvolution of multiple nucleic acid amplifications for the same sample at the same time. The systems can capture and amplify two or more different nucleic acids of interest in a first amplification accumulating two or more different amplification oligomers and detecting the oligomers separately, e.g., at different solid support locations in a second amplification and detection. The system can include two or more different amplification multimers that each accumulate a different amplification oligomer in association with different nucleic acids of interest present in a sample. For example, the system can include a first amplification multimer that hybridizes directly or indirectly to a first nucleic acid of interest and has one or more first M-2 sequences different from second M-2 sequences of a second amplification multimer that hybridizes to the second of the different nucleic acid sequences of interest, so that the two nucleic acids of interest can be separately amplified to accumulate different amplification oligomers. A first amplification oligomer can comprise a sequence complimentary to the first M-2 sequence and comprise a sequence complimentary to a first C-3 or C-2 sequence, and a second amplification oligomer can comprising a sequence complimentary to the second M-2 sequence and comprise a sequence complimentary to a second C-3 or C-2 sequence so that the presence or absence of the first nucleic acid of interest can be detected based on detectable hybridization of the first amplification oligomer to the first C-3 or C-2 sequence, and/or the presence or absence of the second nucleic acid of interest can be detected based on detectable hybridization of the second amplification oligomer to the second C-3 or C-2 sequence. The unique C-2 or C-3 sequence compliments of the amplification oligomers can allow their direction to be captured at specific locations on a solid support of a second amplification. For example, the first C-3 or C-2 sequences can be bound to solid support particles emitting a first identification signal and the second C-3 or C-2 sequences are bound to particles emitting a second identification signal different from the first signal, so that the identity of the particle can be associated with the identity of the nucleic acid of interest present in the sample. Alternately, the first C-3 or C-2 sequences can be bound to a surface of a first chamber and the second C-3 or C-2 sequences are bound a surface of a second chamber, so that signal ultimately detected from the first chamber indicates the presence of the first nucleic acid of interest in the sample, and signal ultimately from the second chamber indicates the presence of the second nucleic acid of interest in the sample. Where matrixed amplification reactions are finally detectable as a signal from an array of beads, a flow cytometer can be used to sort and detect a particle comprising an amplification oligomer; or where the detectable signal is ultimately provided at an array location on a solid support, a charge coupled device can be useful for imaging a location of an amplification oligomer in a second amplification.

In another aspect of multiplexed two-stage amplifications, the signal produced in the second amplification can be deconvoluted by distinguishing between two or more different signals emanating from the same solid support location. For example, two or more different amplification oligomers previously accumulated and melted from a first amplification solid support can be identified by providing a first label system with a first sequence complimentary to a first label probe comprising a first detectable marker; providing a second label system comprising a second sequence complimentary to a second label probe comprising a second detectable marker different from the first detectable marker; providing a sample from the first amplification in which a first amplification oligomer is capable of hybridizing to a component of the first label system, or which sample comprises or is suspected of comprising a second amplification oligomer capable of hybridizing to a component of the second label system; hybridizing the sample with the first and second label system; and, detecting a signal from the first detectable marker or from the second detectable marker. If a signal is detected from the first detectable marker, the presence of the first amplification oligomer in the sample is indicated. If a signal is detected from the second detectable marker, the presence of the second amplification oligomer in the sample is indicated. In preferred embodiments of this multiplexed amplification, the first and/or second label system comprises: a) a label probe comprising a sequence complimentary to an amplification multimer having a sequence complimentary to a label extender, and the label extender also has a sequence complimentary to the first or the second amplification oligomer, b) a label probe comprising a sequence complimentary to an amplification multimer, which amplification multimer comprises a sequence complimentary to the amplification oligomer, and/or c) a label probe comprising a sequence complimentary to an amplifier, which amplifier comprises a sequence complimentary to a preamplifier, which preamplifier comprises a sequence complimentary to the amplification oligomer. In many embodiments, it is preferred that label system accomplishes hybridization to the amplification oligomers indirectly, e.g., through label extenders. The first and second label systems can have the same type of label but with different distinguishable signals, or the first and second label systems can have different types of labels. For example, different label types can be fluorophores, radionuclides, ligands, enzymes, chromophores, chemiluminescent compounds, and/or the like. The different distinguishable signals can be fluorescent or chemiluminescent emissions at different frequencies, intensities, or combinations of frequencies; radionuclides emitting different particles or with different energies; ligands with different reporters; enzymes with different substrates or products; chromophores with different absorbances, and/or the like. In an aspect of multiplex deconvolution, the present invention provides identification of two or more amplification oligomers at substantially the same location by detecting both a first and second label probe at the location. Optionally, identification is provided for two or more amplification oligomers at the same time by detecting both the first and second detectable marker at substantially the same time; optionally, at the same solid support location.

In still another aspect of multiplexed two-stage amplifications, the first amplification takes place at two or more solid support locations with different capture systems. The capture systems can uniquely hybridize with different nucleic acids of interest. In this way, different target nucleic acids of interest from the same sample can be captured separately then amplified, e.g., using the same set of amplification multimers and amplification oligomers. After optionally washing away residual components of the first amplification, a second amplification can be provided wherein the amplification oligomers at the separate locations act as the target nucleic acid input to accumulate detectable label probes at the locations. In one embodiment, the solid support locations are on separate beads having identifying signals. After the first hybridization, the beads can be separated to different positions for individual second amplifications and detections. In one embodiment using first captures of target nucleic acids at separate or separable locations, the nucleic acids of interest are detected by: a) providing a sample comprising or suspected of comprising one or more nucleic acids of interest; b) providing a first solid support which comprises first capture extender sequence or first capture probe sequence complimentary to a first nucleic acid of interest; c) providing a second solid support which comprises a second capture extender sequence or a second capture probe sequence complimentary to a second nucleic acid of interest; d) contacting the first and second solid supports with the sample; e) capturing the first nucleic acid of interest on the first solid support and/or capturing the second nucleic acid of interest on the second solid support; f) hybridizing a first labeling system directly or indirectly to the first and/or second nucleic acid of interest; g) hybridizing the first labeling system to one or more amplification oligomers; h) separating the first solid support from the second solid support; and i) separately detecting the previously hybridized amplification oligomers on each solid support in a nucleic acid assay. This technique allows two or more different target nucleic acids of interest to be separately detected and quantitated using unique capture systems but common amplification and detection systems.

In two-stage multiplexed amplifications where the first amplification solid supports are separate or separable, the detection of the first amplification can be through a bDNA assay, PCR, LCR, a northern blot, a Southern blot, electrophoresis, light absorbance and/or the like. Separating steps can be accomplished, e.g., by particle sorting, cell sorting, magnetic sorting, and/or the like.

In another aspect of two-stage multiplexed amplifications with separate first amplifications, the amplification oligomers associated through an amplification multimers with the first nucleic acid of interest can be the same amplification oligomers associated with the second nucleic acid of interest, yet the two nucleic acids can still be separately identified. This result follows from the fact that the chain of identity from nucleic acid of interest to label probe signal in this case does not depend on the specific capture of the amplification oligomers at a specific solid support location for the second amplification.

DEFINITIONS

Unless otherwise defined herein or below in the remainder of the specification, all technical and scientific terms used herein have meanings commonly understood by those of ordinary skill in the art to which the present invention belongs.

Before describing the present invention in detail, it is to be understood that this invention is not limited to particular compositions, methods, or systems, which can, of course, vary. It is also to be understood that the terminology used herein is for the purpose of describing particular embodiments only, and is not intended to be limiting. As used in this specification and the appended claims, the singular forms "a", "an" and "the" include plural referents unless the content clearly dictates otherwise. Thus, for example, reference to "a component" can include a combination of two or more components; reference to "a nucleic acid" can include mixtures of nucleic acids, and the like.

Although many methods and systems similar, modified, or equivalent to those described herein can be used in the practice of the present invention without undue experimentation, many preferred materials and methods are described herein. In describing and claiming the present invention, the following terminology will be used in accordance with the definitions set out below.

The term "about" as used herein indicates the value of a given quantity varies by +/−10% of the value, or optionally +/−5% of the value, or in some embodiments, by +/−1% of the value so described.

The term "amplification" in the context of the present inventions, refers to an accumulation of two or more molecules in a system, which accumulation is specifically associated with the presence of a nucleic acid of interest (e.g., target nucleic acid of a sample in a first amplification or amplification oligomer in a second amplification) in the system (e.g., in solution or at a surface). The accumulation can consist of enzymatic replication of copies the nucleic acid of interest. Alternately, the amplification can consist of an accumulation of another molecule (e.g., binding an amplification product nucleic acid to a solid support) dependent on the presence of the nucleic acid of interest. For example, in a typical bDNA assay, the presence of a target nucleic acid of interest in the system can be amplified into a large number of detectable label probes (or amplification oligomers) bound to a solid support in association with the initial presence of the target nucleic acid in a sample. In a typical PCR reaction, the presence of a target nucleic acid of interest in the system can result in the accumulation of a large number of replicate copies and complimentary nucleic acid sequences.

The term "polynucleotide" (and the equivalent term "nucleic acid") encompasses any physical string of monomer units that can be corresponded to a string of nucleotides, including a polymer of nucleotides (e.g., a typical DNA or RNA polymer), peptide nucleic acids (PNAs), modified oligonucleotides (e.g., oligonucleotides comprising nucleotides that are not typical to biological RNA or DNA, such as 2'-O-methylated oligonucleotides), and the like. The nucleotides of the polynucleotide can be deoxyribonucleotides, ribonucleotides or polymers of nucleotide analogs, can be natural or non-natural, and can be unsubstituted, unmodified, substituted or modified. The nucleotides can be linked by phosphodiester bonds, or by phosphorothioate linkages, methylphosphonate linkages, boranophosphate linkages, or the like. The polynucleotide can additionally comprise non-nucleotide elements such as labels, quenchers, blocking groups, or the like. The polynucleotide can be, e.g., single-stranded or double-stranded.

A "polynucleotide sequence" or "nucleotide sequence" is a polymer of nucleotides (an oligonucleotide, a DNA, an RNA, a nucleic acid, etc.) or a character string representing a nucleotide polymer, depending on context. From any specified polynucleotide sequence, either the given nucleic acid or the complementary polynucleotide sequence (e.g., the complementary nucleic acid) can be determined.

Two polynucleotides "hybridize" when they associate to form a stable duplex, e.g., under relevant assay conditions. Nucleic acids hybridize due to a variety of well characterized physico-chemical forces, such as hydrogen bonding, solvent exclusion, base stacking and the like. An extensive guide to the hybridization of nucleic acids is found in Tijssen (1993) Laboratory Techniques in Biochemistry and Molecular Biology-Hybridization with Nucleic Acid Probes, part I chapter 2, "Overview of principles of hybridization and the strategy of nucleic acid probe assays" (Elsevier, N.Y.).

The "Tm" (melting temperature) of a nucleic acid duplex under specified conditions (e.g., relevant assay conditions) is the temperature at which half of the base pairs in a population of the duplex are disassociated and half are associated. The Tm for a particular duplex can be calculated and/or measured, e.g., by obtaining a thermal denaturation curve for the duplex (where the Tm is the temperature corresponding to the midpoint in the observed transition from double-stranded to single-stranded form).

The term "complementary" refers to a polynucleotide that forms a stable duplex with its "complement," e.g., under relevant assay conditions. Typically, two polynucleotide sequences that are complementary to each other have mismatches (mismatched base pairs) at less than about 20% of the bases, at less than about 10% of the bases, preferably at less than about 5% of the bases, one mismatch, and more preferably have no mismatches.

A "capture probe" or "CP" is a polynucleotide attached to a solid support and comprises a sequence useful to directly or indirectly specifically capture a particular nucleic acid of interest. For example, a capture probe can specifically hybridize to a capture extender (and/or can include a sequence complimentary to a nucleic acid of interest, e.g., to directly and specifically capture the nucleic acid of interest) and that is tightly bound (e.g., covalently or non-covalently, directly or through a linker, e.g., streptavidin-biotin or the like) to a solid support, a spatially addressable solid support, a slide, a particle, a microsphere, a bead, or the like. The capture probe typically comprises at least one polynucleotide sequence C-2 that is complementary to polynucleotide sequence C-1 of at least one capture extender (or, in systems designed for direct capture of a nucleic acid of interest, the C2 sequence can be complimentary to a sequence of the nucleic acid of interest). The capture probe is preferably single-stranded.

A "capture extender" or "CE" is a polynucleotide (or comprises a polynucleotide) that is capable of hybridizing to a nucleic acid of interest and to a capture probe. A capture extender can bind a particular nucleic acid of interest to a particular solid support, through a capture probe, with high specificity. The capture extender typically has a first polynucleotide sequence C-1, which is complementary to the capture probe, and a second polynucleotide sequence C-3, which is complementary to a polynucleotide (target) sequence of the nucleic acid of interest. Sequences C-1 and C-3 are typically not complementary to each other. The capture extender is preferably single-stranded.

A "label extender" or "LE" is a polynucleotide that is capable of hybridizing to a nucleic acid of interest and to a label probe system. A capture extender can link a particular nucleic acid of interest to components of a label system. The label extender typically has a first polynucleotide sequence L-1, which is complementary to a polynucleotide sequence of the nucleic acid of interest, and a second polynucleotide sequence L-2, which is complementary to a polynucleotide sequence of the label probe system (e.g., L-2 can be complementary to an M-1 polynucleotide sequence of an amplification multimer, a preamplifier, a label probe, or the like). The label extender is preferably single-stranded.

A "label" is a moiety that facilitates detection of a molecule (e.g., by providing a detectable signal). Common labels in the context of the present invention include fluorescent, luminescent, light-scattering, and/or colorimetric labels. Suitable labels include enzymes and fluorescent moieties, as well as radionuclides, substrates, cofactors, inhibitors, chemiluminescent moieties, magnetic particles, and the like. Patents teaching the use of such labels include U.S. Pat. Nos. 3,817,837; 3,850,752; 3,939,350; 3,996,345; 4,277,437; 4,275,149; and 4,366,241. Many labels are commercially available and can be used in the context of the invention.

A "label probe" or "LP" is a single-stranded polynucleotide that comprises a label (or optionally that is configured to bind to a label) that directly or indirectly provides a detectable signal. The label probe typically comprises a polynucleotide sequence that is complementary to the repeating polynucleotide sequence M-2 of an amplification multimer. Optionally, a label probe can hybridize directly to a sequence on the nucleic acid of interest (e.g., an amplification oligomer). However, in most cases, label probes are not designed to hybridize directly to the nucleic acid of interest.

A "label probe system", in the context of the present inventions, comprises one or more polynucleotides that can hybridize (through a label extender or not), to associate one or more labels with a nucleic acid of interest. The nucleic acid of interest can be, e.g., a target nucleic acid of interest in a sample or an amplification oligomer target of a second amplification of the methods. For example, a label probe system can comprise a combination of label extenders, amplification multimers, preamplifiers, amplifiers and/or label probes. In one embodiment, the label probe system comprises an amplification multimer with an M-1 sequence complementary to a label extender and a plurality of M-2 sequences complimentary to a label probe sequence. Optionally, the label probe system comprises a preamplifier with a sequence complimentary to a label extender L-2 sequence and replicate sequences complimentary to an amplifier sequence, which amplifier also has replicate sequences complimentary to a label probe sequence. One or more polynucleotide sequences M-1 of the label probe system are optionally identical sequences or different sequences. Optionally, the label probe system hybridizes directly to a nucleic acid of interest without a label extender. Alternately, the label probe system is simply a label probe with a sequence complimentary to a nucleic acid of interest (or not). The label probe system can include a plurality of label probes (e.g., a plurality of identical label probes, probes of different types, or probes of the same type but providing different detectable signals).

A "complex" in the context of amplifications of the invention, refers to three or more amplification components (e.g., capture probes, capture extenders, label extenders, amplification multimers, amplification oligomers, or label probes) bound together through hybridization of complimentary sequences.

"Different" polynucleotides have different sequences. For example, a polynucleotide or polynucleotide sequence is different from another if they do not have 100% sequence identity, have less that 99% identity, less that 95% identity less than 90% identity or less than 80% sequence identity.

Polynucleotides are "captured" when they are bound directly or indirectly (e.g., through hybridization to an extender or as part of a complex) to a solid support.

Polynucleotides are "indirectly" associated (e.g., hybridized, captured, bound) with a solid support or another identified polynucleotide when the association comprises linkage through one or more other polynucleotide, such as, e.g., a capture extender or label extender.

An "amplification multimer" is a polynucleotide comprising a sequence directly complimentary to a nucleic acid of interest (or indirectly specifically hybridizable to the nucleic acid of interest, e.g., through a label extender) and comprising a plurality of substantially identical polynucleotide sequences complimentary to label probes (or to amplification oligomers, in the case of a first amplification of a two-stage amplification). The amplification multimer has a structure designed to function by specifically associating multiple label probes or amplification oligomers with a nucleic acid of interest. For example, amplification multimers can have an M-1 polynucleotide sequence complimentary to a nucleic acid of interest and a plurality of M-2 sequences complimentary to label probes, e.g., to specifically bind multiple labels to the nucleic acid of interest (e.g., an amplification oligomer). Alternately, amplification multimers can have an M-1 polynucleotide sequence complimentary to a nucleic acid of interest (e.g., a test sample nucleic acid) and a plurality of sequences M-2 complimentary to amplification oligomers, e.g., to specifically accumulate multiple amplification oligomers in association with the nucleic acid of interest. In many embodiments of two-stage non-enzymatic amplifications of the invention, a first amplification multimer of a first amplification stage comprises an M-1 sequence complimentary to a sample target nucleic acid of interest (or indirectly hybridizable to the sample target nucleic acid of interest through a label extender) and multiple replicate M-2 sequences complimentary to an amplification oligomer; and, a second amplification multimer of a second stage amplification comprising an M-1 sequence complimentary to the amplification oligomer (or indirectly hybridizable to the amplification oligomer through a label extender) and multiple replicate M-2 sequences complimentary to a label probe. The M-1 sequence of the amplification is not necessarily attached to the replicate M-2 sequences solely through covalent bonds (i.e., M-2 sequences of an amplification multimer can be associated with M-1 sequences through non-covalent interactions, such as, e.g., polynucleotide hybridizations, affinity interactions, and/or the like). For example, an amplification multimer can comprise a preamplifier complimentary to a label extender (or target nucleic acid) and an amplifier complimentary to the preamplifier and multiple label probes (or amplification oligomers). The amplification multimer can be, e.g., a linear or a branched nucleic acid. As noted for all polynucleotides, the amplification multimer can include modified nucleotides and/or nonstandard internucleotide linkages as well as standard deoxyribonucleotides, ribonucleotides, and/or phosphodiester bonds. Suitable amplification multimers are described, for example, in U.S. Pat. Nos. 5,635,352, 5,124,246, 5,710,264, and 5,849,481.

An amplification oligomer can be designed to have sequences allowing it to function both as the amplification product of a first branched DNA amplification and as the input target of a second nucleic acid amplification. As used herein with regard to a two-stage amplification method, the term "amplification oligomer" refers to a polynucleotide comprising a sequence complimentary to the repeat sequences amplification multimers employ to accumulate polynucleotides (e.g., amplification multimer repeat sequences analogous to those that capture label probes in classic bDNA assays, e.g., M-2 sequences) of a first bDNA amplification and also comprising sequences complimentary to 1) a label system component (e.g., label extenders (e.g., at L-1) or amplification multimers (e.g., at M-1)) of a second bDNA amplification, or 2) one or more primer oligomers of an enzymatic amplification technique. An amplification oligomer can be designed with sequences allowing it to function as both the amplification product of a first bDNA amplification and as the target nucleic acid of interest in a second bDNA amplification. For example, in the context of non-enzymatic two-stage amplifications of the invention an "amplification oligomer" is designed to function in a stringent hybridization with at least two sequence replicates of the amplification multimer of the first amplification and also designed to function in a stringent hybridization to capture the label system complex of the second amplification.

A "preamplifier" is a nucleic acid that serves as an intermediate between one or more label extenders and amplifiers. Typically, the preamplifier is capable of hybridizing simultaneously to at least two label extenders and to a plurality of amplifiers.

Branched DNA technology used in the methods can include amplification methods that employ label systems that hybridize directly or indirectly to a target nucleic acid and associate multiple copies of another nucleic acid (e.g., label probes or amplification oligomers) to the target nucleic acid. It is worth noting that the amplification multimer is typically, but not necessarily, a branched-chain nucleic acid; for example, the amplification multimer can be a branched, forked, or comb-like nucleic acid or a linear nucleic acid, or a complex thereof. Typically branched DNA of the present invention includes a nucleic acid having a "trunk" structure covalently attached to multiple nucleic acid branches having multiple sequences complimentary to, e.g., label probes. For example, see amplification multimers. Alternately, the branches of the branched DNA label systems can be attached to a "trunk" by affinity or hybridization systems to ultimately associate the multiple sequences to the target nucleic acid. For example, see labeling systems, described herein, comprising label extenders complimentary to preamplifiers complimentary to amplifiers complimentary to label probes.

BRIEF DESCRIPTION OF THE DRAWINGS

FIGS. 5A through 5G, present schematic diagrams of a multiplexed two-stage amplification using a planar solid support in the first amplification and microsphere solid supports in the second amplification.

FIG. 6 is a schematic diagram showing how signals detected from a multiplexed two-stage amplifying can be deconvoluted to unambiguously associate the signals with the presence of a particular nucleic acid in a sample.

DETAILED DESCRIPTION

The present invention provides methods and systems using amplification oligomers in a two-stage amplification scheme that can detect the presence of a nucleic acid of interest with improved sensitivity and consistency in a complex sample. Amplification oligomers are nucleic acids comprising, e.g., sequences designed to be accumulated at a solid support by hybridization to repetitive complimentary sequences in a first non-enzymatic amplification and also comprising sequences acting as the target sequence for a second amplification system or nucleic acid assay. The accumulation of the amplification oligomer in the first amplification is dependent on the presence of a target nucleic acid of interest in a sample so that a detection signal from the second amplification or assay correlates to the presence of the target nucleic acid in the sample. Two-stage amplifications of the invention can dramatically enhance the sensitivity for target nucleic acid detection. Information designed into the amplification oligomers can allow multiplexed assays that provide sensitive detection and quantitation of two or more target nucleic acids from the same sample at once.

Methods and systems using amplification oligomers can enable separate identification and quantitation of two or more nucleic acids of interest from the same sample at the same time. For example, two different amplification oligomers, representing two different target nucleic acids of interest, can be enriched in a first amplification. Unique "zip code" sequences in each different amplification oligomer (e.g., sequences complimentary to predesignated capture probes) can allow capture and amplification of the different amplification oligomers at different solid support locations. Thus, the different amplification oligomers, representing target nucleic acids from the same sample, can be separately amplified, identified and quantitated.

Two-Stage Amplifications Detecting Nucleic Acids of Interest

Two-stage amplification methods of the invention generally include a non-enzymatic amplification seeded by a target nucleic acid of interest followed by another non-enzymatic amplification seeded by the amplification product of the first amplification. Typically, the amplification product of the first amplification is an amplification oligomer, e.g., having sequences useful in targeting the oligomer to an intended solid support and having sequences capable of specifically interacting with a second amplification system. Optionally, the second amplification can be an enzymatic amplification known in the art, e.g., to replicate target nucleic acids. The present invention is not limited to these preferred embodiments and can be practiced in a variety of ways.

Figure 1:
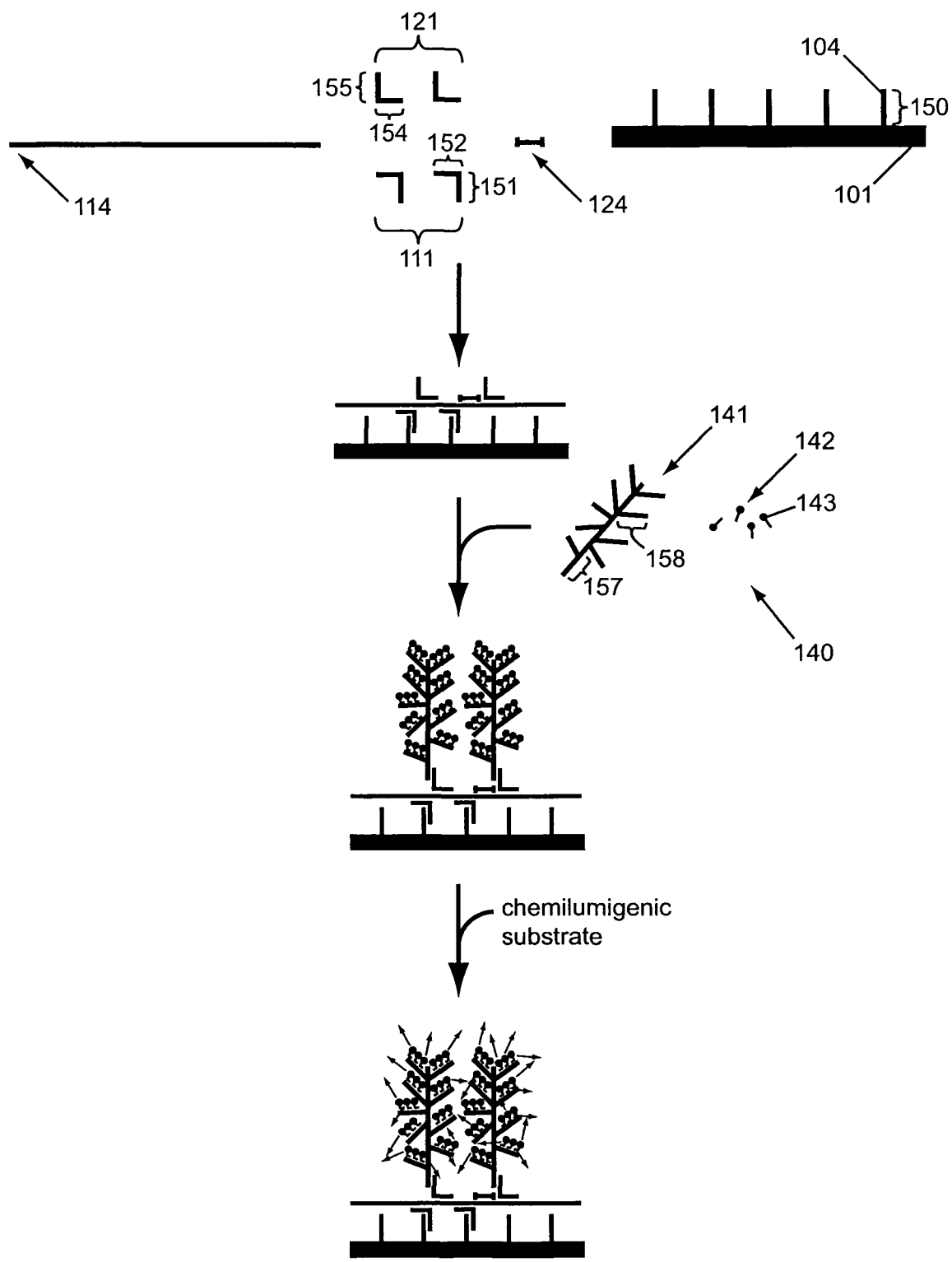
FIG. 1 shows a schematic diagram of an exemplary old art bDNA assay system.

In many embodiments of the methods at least the first amplification stage relies on branched DNA (bDNA) technology. In a typical case of a bDNA amplification, shown in FIG. 1, e.g., a target nucleic acid 114 is captured by a capture extender 111 associated with a solid support 101, the target is decorated at one or more locations with label extenders 121 typically associated with branched DNA molecules 141 capable of binding multitude label probes 142 to generate a large signal associated with the initial capture of a small amount of target.

Figure 2A:
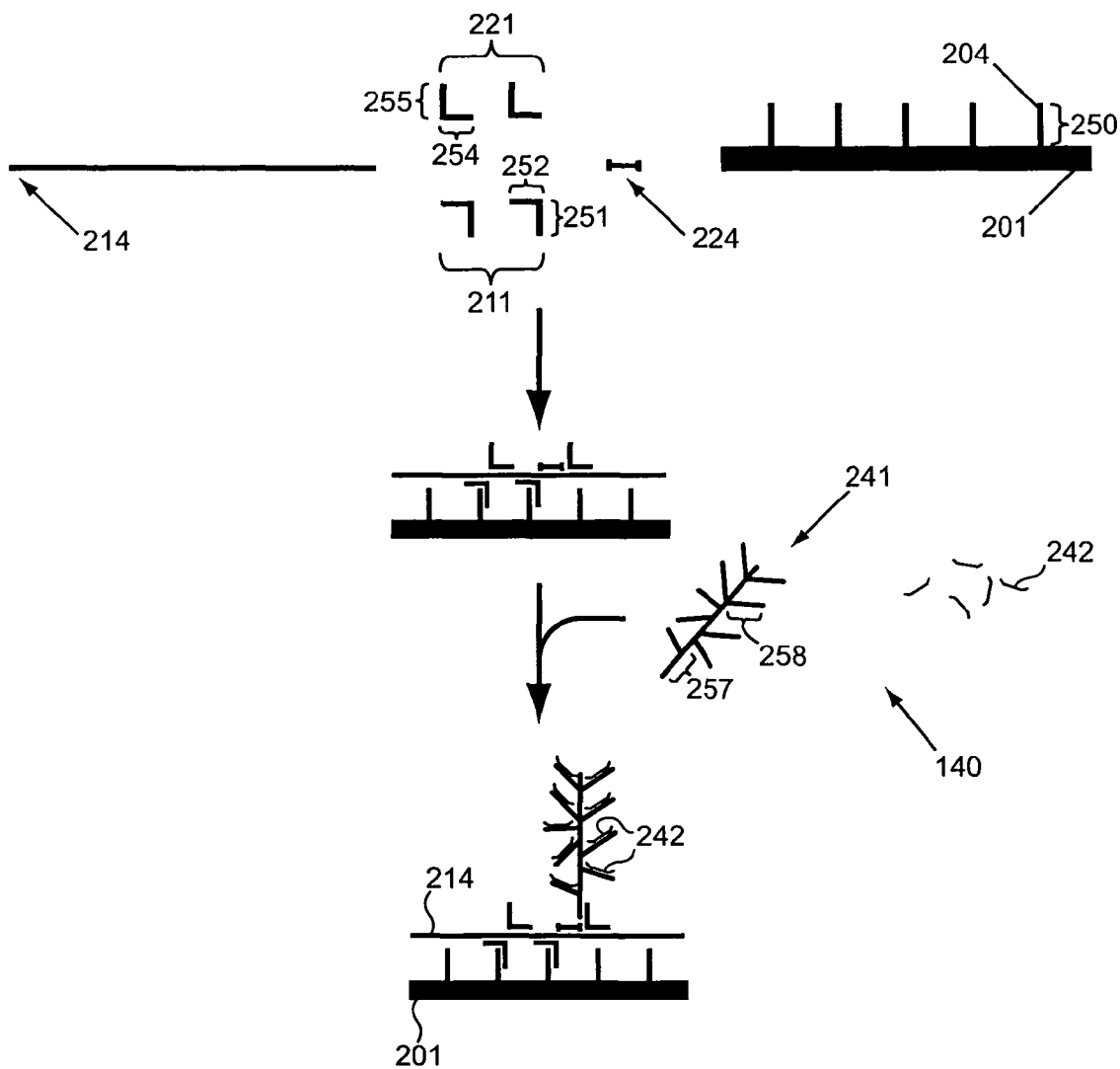
FIGS. 2A and 2B show schematic diagrams depicting a two-stage amplification. In the first amplification of FIG. 2A, target nucleic acid of interest is amplified in a bDNA amplification to accumulate a multitude of amplification oligomers. In the second amplification of FIG. 2B, one of the amplification oligomers from the first amplification stage is amplified in a bDNA amplification accumulating a multitude of label probes.

In the present invention, amplification oligomers are the product of a first amplification dependent on the presence of the target nucleic acid instead of a label probe product. The large amount of amplification oligomers accumulated in association with the target nucleic acid in the first amplification stage can then act as the target nucleic acid in a second amplification. For example, as shown in FIG. 2A, a target nucleic acid 214 is captured from a sample onto a solid support 201. An amplification multimer 241 can then be captured on the solid support by hybridization to complimentary target nucleic acid sequences. The amplification multimer can, in turn, capture a large number of amplification oligomers 242. With the amplification oligomer product captured at the first solid support, the hybridization solution and unbound components of the first amplification system can be washed away with wash solutions at temperatures of appropriate stringency. Then, the amplification oligomers can be melted from the first solid support and transferred to a second amplification system, e.g., associated with a second solid support.

Figure 2B:
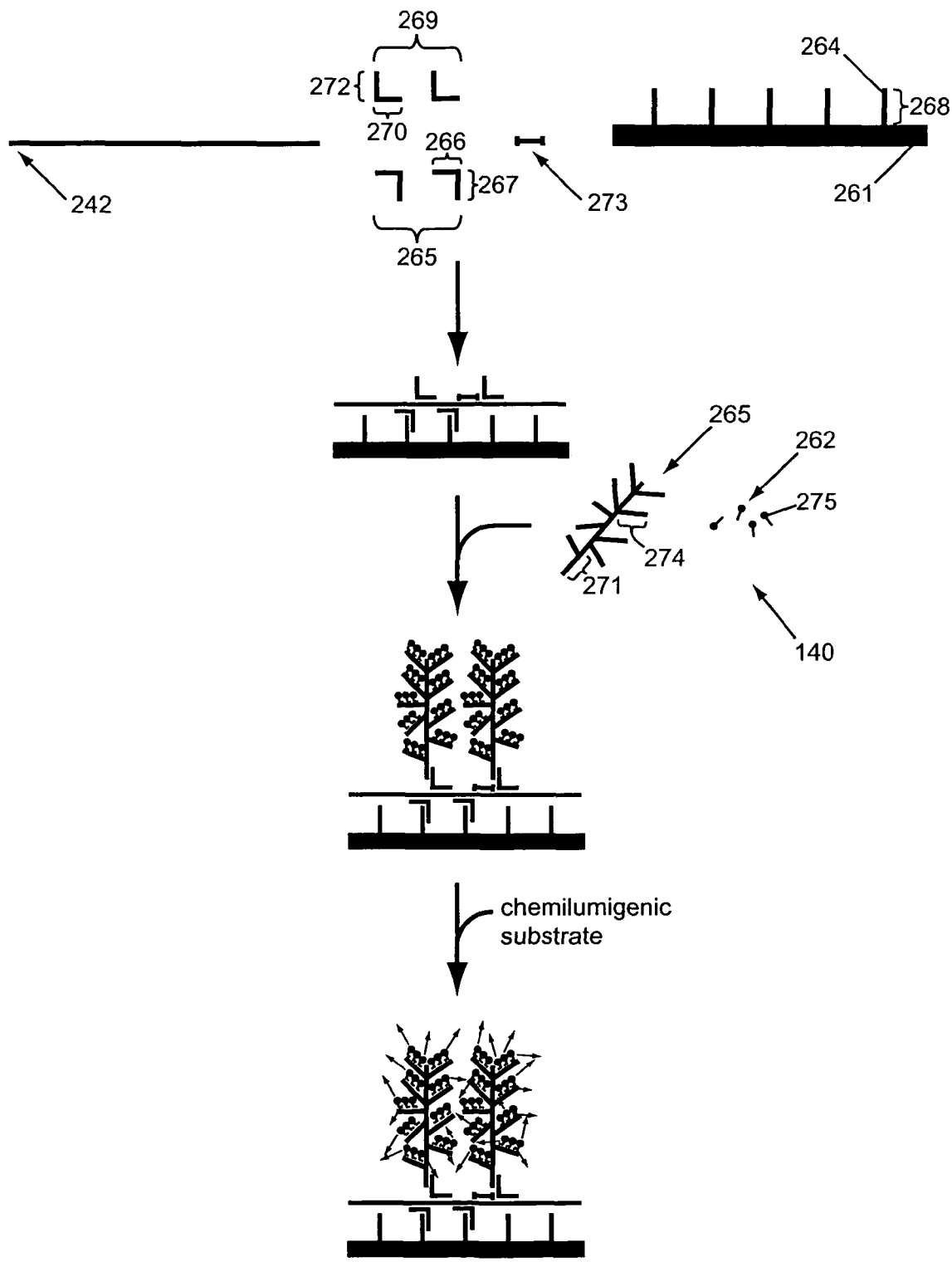

As shown in FIG. 2B, the amplification oligomer can act as the target nucleic acid in the second amplification to accumulate a large number of labeled probes. The signal from these label probes provides a highly sensitive determination of target nucleic acid in the initial sample. For example, Amplification oligomer 242 transferred to the second amplification system can be captured by hybridization to the second solid support 261 through sequences complimentary to capture probes 264 on the solid support. Amplification multimers 265 can be captured by hybridization to sequences complimentary to the captured amplification oligomers and label probes 262 can be captured in large numbers at complimentary sequences of the amplification multimer.

Figure 3A:
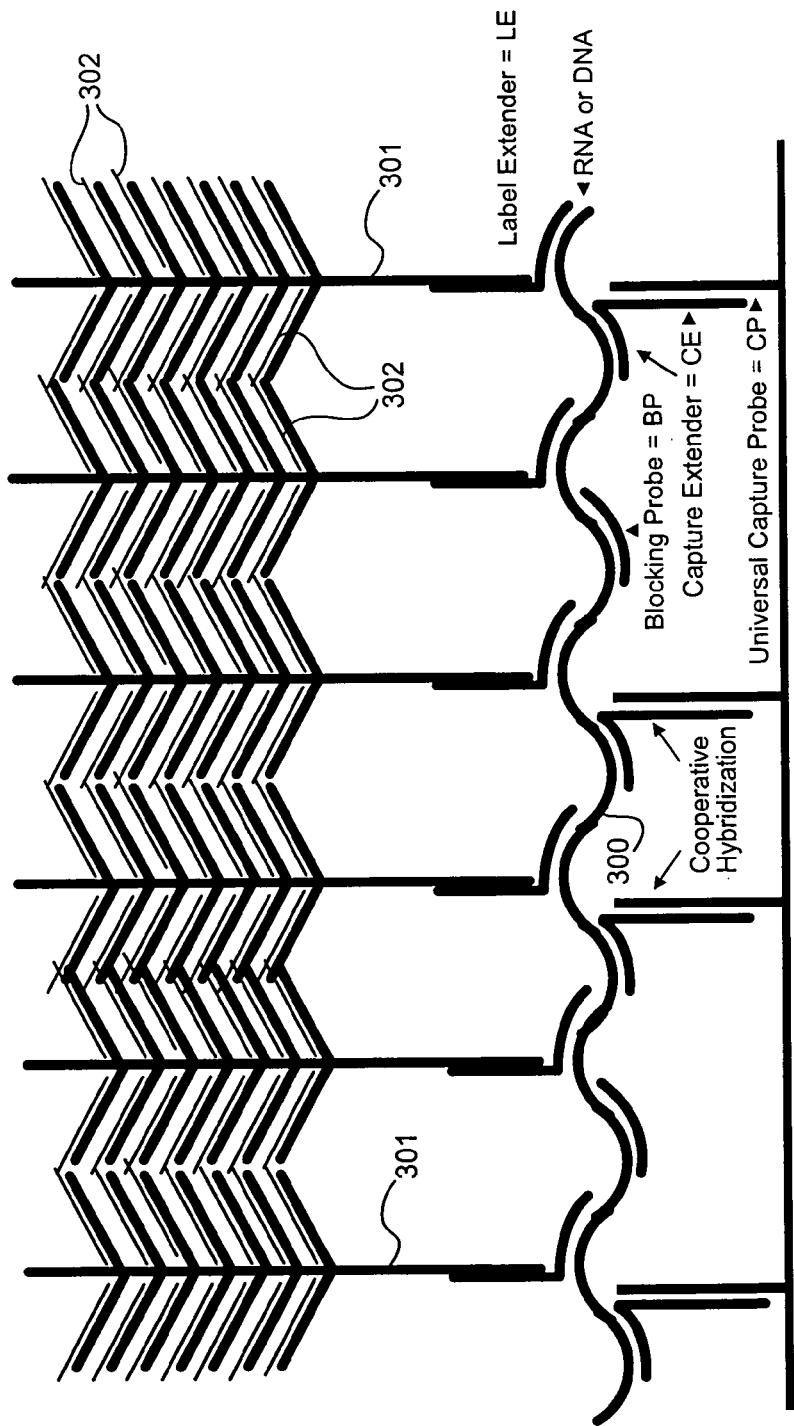
FIGS. 3A and 3B are schematic diagrams showing an exemplary two-stage amplification employing cooperative hybridization and multiple amplification multimers for each captured target nucleic acid of interest.
Figure 3B:
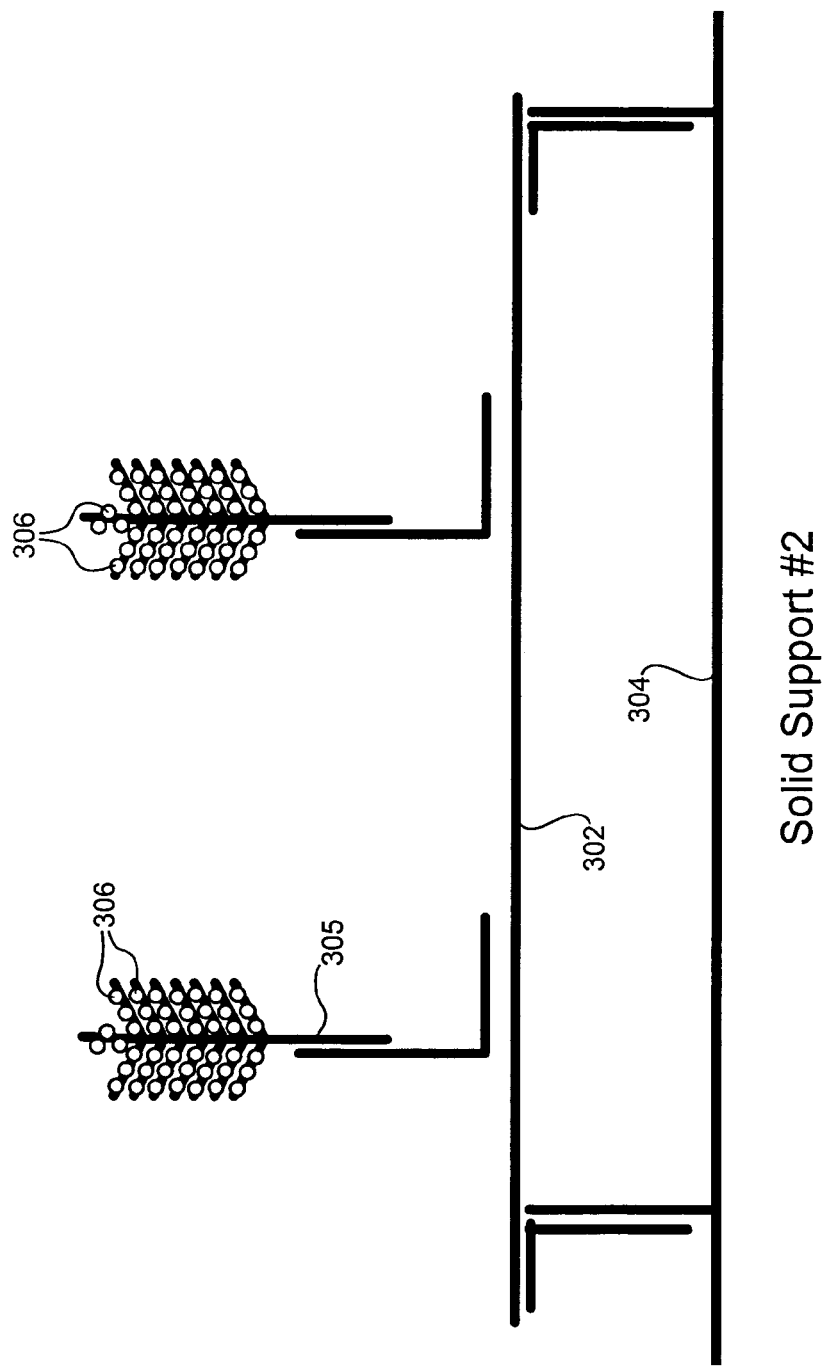

Through the course of the two amplifications, a single target nucleic acid of interest captured from the sample on the first solid support can ultimately lead to the specific capture of many-fold more label probes in the second amplification. For example, as shown in FIG. 3A, in a first amplification, a single target nucleic acid molecule of interest 300 can capture, e.g., six amplification multimers 301. Each amplification multimer can capture, e.g., 14 amplification oligomers 302, for an initial 84-fold amplification of the target to amplification oligomers. As shown in FIG. 3B, the amplification oligomers 302 of the first amplification can be transferred, e.g., to be captured on a second solid support 304 to act as a nucleic acid of interest in a second amplification. Here, one amplification oligomer 302, of the 84 accumulated in the first amplification, can capture, e.g., two amplification multimers 305, which can accumulate 45 label probes 306 each, for a 90-fold amplification of each amplification oligomers to label probe amplification product. Over all, through two amplifications in this example, there has been a 756-fold (84×90) molecular amplification from the sample target nucleic acid to the label probes. One skilled in the art will appreciate that further amplification can be obtained, e.g., by increasing the number of amplification multimers captured in the first and/or second amplification, increasing the number of replicate sites complimentary to amplification oligomers on the first amplification multimers, and/or increasing the number of replicate sites complimentary to label probes on the second amplification multimers. Furthermore, one skilled in the art will appreciate that further amplification can be obtained by inserting one or more additional amplifications between the first and second amplifications wherein the accumulated amplification oligomers of the first amplification function as target for the inserted amplification and the product of the inserted amplification is an amplification oligomer functioning as target for a subsequent amplification.

In the preceding example, label probe system comprises the second amplification multimer and the label probes (with optional label extenders). In other embodiments, the label probe system could comprise a preamplifier system, e.g., as described in U.S. Pat. No. 5,635,352 and 5,681,697, which can typically provide even larger amplification factors at each amplification. In yet another example, the label extenders hybridize directly to the label probes and no amplification multimer or preamplifier is used, so the signal from a single target nucleic acid molecule is only amplified by the number of distinct label extenders that hybridize to that nucleic acid.

Basic bDNA assays have been well described and used, e.g., to detect taggants, to analyze forensic samples, to detect and quantify mRNA transcripts in cell lines, to determine viral loads, and the like. The bDNA assay provides reliable direct quantification of nucleic acid molecules at physiological levels. Several advantages of the technology distinguish it from other DNA/RNA amplification technologies, including linear amplification, good sensitivity and dynamic range, great precision and accuracy, simple sample preparation procedure, and reduced sample-to-sample variation. For additional details on bDNA assays, see, e.g., U.S. Pat. No. 4,868,105 to Urdea et al. entitled "Solution phase nucleic acid sandwich assay"; U.S. Pat. No. 5,635,352 to Urdea et al. entitled "Solution phase nucleic acid sandwich assays having reduced background noise"; U.S. Pat. No. 5,681,697 to Urdea et al. entitled "Solution phase nucleic acid sandwich assays having reduced background noise and kits therefore"; U.S. Pat. No. 5,124,246 to Urdea et al. entitled "Nucleic acid multimers and amplified nucleic acid hybridization assays using same"; U.S. Pat. No. 5,624,802 to Urdea et al. entitled "Nucleic acid multimers and amplified nucleic acid hybridization assays using same"; U.S. Pat. No. 5,849,481 to Urdea et al. entitled "Nucleic acid hybridization assays employing large comb-type branched polynucleotides"; U.S. Pat. No. 5,710,264 to Urdea et al. entitled "Large comb type branched polynucleotides"; U.S. Pat. No. 5,594,118 to Urdea and Horn entitled "Modified N-4 nucleotides for use in amplified nucleic acid hybridization assays"; U.S. Pat. No. 5,093,232 to Urdea and Horn entitled "Nucleic acid probes"; U.S. Pat. No. 4,910,300 to Urdea and Horn entitled "Method for making nucleic acid probes"; U.S. Pat. Nos. 5,359,100; 5,571,670; 5,614,362; 6,235,465; 5,712,383; 5,747,244; 6,232,462; 5,681,702; 5,780,610; 5,780,227 to Sheridan et al. entitled "Oligonucleotide probe conjugated to a purified hydrophilic alkaline phosphatase and uses thereof"; U.S. patent application Publication No. US2002172950 by Kenny et al. entitled "Highly sensitive gene detection and localization using in situ branched-DNA hybridization"; Wang et al. (1997) "Regulation of insulin preRNA splicing by glucose" Proc Nat Acad Sci USA 94:4360-4365; Collins et al. (1998) "Branched DNA (bDNA) technology for direct quantification of nucleic acids: Design and performance" in Gene Quantification, F Ferre, ed.; and Wilber and Urdea (1998) "Quantification of HCV RNA in clinical specimens by branched DNA (bDNA) technology" Methods in Molecular Medicine: Hepatitis C 19:71-78. In addition, reagents for performing basic bDNA assays (e.g., QuantiGene™ kits, amplification multimers, alkaline phosphatase labeled label probes, chemilumigenic substrate, capture probes immobilized on a solid support, and the like) are commercially available, e.g., from Panomics, Inc. (on the world wide web at www.panomics.com), and can be adapted for the practice of the present invention. Software for designing probe sets for a given nucleic acid target (i.e., for designing the regions of the capture extenders, label extenders, and optional blocking probes that are complementary to the target) is also commercially available (e.g., ProbeDesigner™ from Panomics, Inc.); see also Bushnell et al. (1999) "ProbeDesigner: for the design of probe sets for branched DNA (bDNA) signal amplification assays Bioinformatics 15:348-55.

In some embodiments of the methods, the second amplification can be an enzymatic amplification. For example, the amplification oligomer product of the first amplification can be input as a target nucleic acid in a ligase chain reaction (LCR) or polymerase chain reaction (PCR) for the second amplification and detection. In a preferred embodiment, accumulated amplification oligomers from a first branched chain amplification can be melted from the amplification multimers and transferred to a PCR reaction chamber. In PCR amplifications, the amplification oligomer can function as the PCR template region to be amplified. Two or more different primers are included in the PCR reaction solution to determine the beginning and end of the region to be amplified. Taq polymerase can then incorporate and nucleotide triphosphates to copy the region between the primers by primer extensions. The PCR process is carried out in a thermal cycler that heats and cools the reaction chamber according to a programmable temperature profile cycle required for target melting, primer hybridization to target, primer extension, and replicate melting. The cycle typically continues up to about 35 cycles for an amplification ranging from about $10^3$ to about $10^6$-fold. The amplification product can be detected, e.g., by incorporation or labeled nucleotides into the amplification products during the primer extensions, or by other conventional means, such as, e.g., northern blotting, a Southern blotting, electrophoresis, 280 nm absorbance, and the like.

Samples Containing Target Nucleic Acids of Interest

The two-stage amplification methods of the invention can amplify, and ultimately detect nucleic acids of interest with high sensitivity from complex sample materials. The nucleic acids can be any type of interest, such as, e.g., DNA, cDNA, rRNA, mRNA, miRNA, etc.

The methods can be used to detect the presence of the nucleic acids of interest in essentially any type of sample. For example, the sample can be derived from an animal, a human, a plant, a cultured cell, a virus, a bacterium, a pathogen, and/or a microorganism. The sample optionally includes a cell lysate, an intercellular fluid, a bodily fluid (including, but not limited to, blood, serum, saliva, urine, sputum, or spinal fluid), and/or a conditioned culture medium, and is optionally derived from a tissue (e.g., a tissue homogenate), a biopsy, and/or a tumor. As just a few examples, the nucleic acids of interest can be derived from one or more of an animal, a human, a plant, a cultured cell, a microorganism, a virus, a bacterium, or a pathogen. The use of a bDNA type amplification can have a great advantage over many enzymatic amplifications for such complex and impure samples because hybridizations are less sensitive to interference than typical amplification enzymes. With the bulk of the complex sample washed away after the first amplification, the first amplification product can be far more compatible with second amplification systems, including enzymatic amplification systems.

The methods can amplify and detect nucleic acids of interest known to be in a sample (e.g., to provide quantitative results) and/or the methods can detect the presence of a nucleic acid of interest suspected of being present in a sample. To test for the presence of a nucleic acid suspected of being in a sample, the first amplification stage, e.g., would provide capture extenders and label extenders complimentary to that sample nucleic acid of interest. If the nucleic acid of interest is present in the sample, the first amplification would be productive and provide amplification oligomers in amounts adequate to provide a positive signal in the second amplification. If the nucleic acid of interest is not present in the sample, or is present in amounts below the sensitivity of the two-stage amplification system, inadequate amounts of amplification oligomer wound be accumulated in the first amplification and no positive signal above background levels would be detected for the second amplification. Thus, the two-stage amplification can be configured to detect a nucleic acid of interest suspected of being present in a sample, and can confirm whether or not the nucleic acid is actually present with a high sensitivity.

The methods can be used to quantitatively detect nucleic acids of interest in samples, e.g., for gene expression analysis. Accordingly, in one class of embodiments, the one or more nucleic acids of interest comprise one or more mRNAs. A standard curve of, e.g., signal output from the second amplification versus known amounts of mRNA input to the first amplification can be prepared. The output signal associated with the one or more mRNAs can be compared to the standard curve to determine the amount of the mRNAs in an unknown sample, as is known in the art.

Capturing Nucleic Acids

In many methods of the invention, nucleic acids of interest are captured on a solid support, e.g., in a step of the first and/or second amplification. The nucleic acids are typically in a purified or crude solution, allowing them to kinetically interact with groups associated with a solid support surface. The nucleic acids of interest can be captured directly or indirectly, specifically or non-specifically. In preferred embodiments, the nucleic acids are captured at the solid support of the first amplification indirectly (e.g., through capture extenders) with a high degree of specificity (e.g., under stringent hybridization conditions).

Nucleic acids of interest can be captured on a solid support directly and non-specifically. For example, the nucleic acids can be captured through chemical reactions or non-specific chemical interactions between the solid support and the nucleic acid. The solid support can include reactive groups that form covalent bonds to bases, or preferably the sugar-phosphate chain of the nucleic acid. The solid support can include chemical groups that interact with the nucleic acids through non-covalent forces, such as, e.g., ionic interactions, hydrophobic interactions, chelation, Van der Waals forces, polar interactions, and/or the like. A typical solid support for direct non-specific capture of nucleic acids can be, e.g., nitrocellulose or nylon membranes otherwise used in dot-blot or Southern blot analyses. Direct, non-specific capture is most appropriate, e.g., when the sample is relatively pure and/or the nucleic acid of interest is expected to be a predominant nucleic acid in the sample. In methods using direct, non-specific capture, it can be important to block the solid support, e.g., with sheared salmon sperm DNA and/or the like, to avoid generation of non-specific background signals.

In other embodiments, the nucleic acids of interest can be captured directly and specifically on a solid support. For example, the solid support can comprise a nucleic acid (e.g., capture probe) on the surface, which has sequences complimentary to the nucleic acid of interest. Exposure of the nucleic acid of interest, in a sample solution adjusted to appropriate stringency, to a capture probe on the solid support can result in capture by specific hybridization directly with the solid support. Such an arrangement is capable of capturing the nucleic acid of interest from a complex sample, such as a lysate, even if the nucleic acid of interest represents only a small minority of the nucleic acids in the sample. Optionally, nucleic acids, (e.g., comprising haptens or protein binding sites) can be captured specifically and directly by nucleic acid binding proteins or antibodies.

In still other embodiments, the nucleic acid of interest can be captured indirectly and specifically. In a preferred embodiment, a single type of solid support has the flexibility to optionally capture various alternate nucleic acids of interest. Such a solid support can have a "universal" capture probe that can hybridize to any number of capture extender oligonucleotides having a sequence complimentary to the capture probe sequence and designed to be specifically to a particular nucleic acid of interest. In this way, the nucleic acid of interest can be captured indirectly, through the capture extender, but specifically through hybridization to the complimentary sequence of the capture extender. The solid support is universal and the capture extender provides specificity to indirectly capture the nucleic acid.

Hybridizing Nucleic Acids

Hybridizing is an important aspect of the first and/or second amplifications in the methods of the invention. Hybridizations between complimentary sequences of amplification reaction components can provide, e.g., the direct or indirect capture of target nucleic acids; the binding interactions of amplification multimers, amplification oligomers and/or label probes; retention of desired components while undesired materials are removed in stringent wash steps; accumulation of substrates for enzyme amplifications; and/or the like.

Nucleic acids "hybridize" when they specifically associate in solution appropriate conditions. Nucleic acids hybridize due to a variety of well characterized physico-chemical forces, such as hydrogen bonding, solvent exclusion, base stacking and the like. An extensive guide to the hybridization of nucleic acids is found in Tijssen (1993) *Laboratory Techniques in Biochemistry and Molecular Biology—Hybridization with Nucleic Acid Probes*, part I, chapter 2, "Overview of principles of hybridization and the strategy of nucleic acid probe assays," (Elsevier, N.Y.), as well as Ausubel et al., eds., *Current Protocols*, a joint venture between Greene Publishing Associates, Inc. and John Wiley & Sons, Inc., (supplemented through 2003). Hames and Higgins (1995) *Gene Probes* 1, IRL Press at Oxford University Press, Oxford, England (Hames and Higgins 1) and Hames and Higgins (1995) *Gene Probes* 2, IRL Press at Oxford University Press, Oxford, England (Hames and Higgins 2) provide details on the synthesis, labeling, detection and quantification of DNA and RNA, including oligonucleotides.

Methods of the invention can be optimized for hybridization and washing stringency through empirical studies, or through calculations of preferred conditions. Stringent hybridization conditions are typically at a temperature near the melting temperature ($T_m$) of the complimentary sequences involved. For example, in the context of the present invention, stringent conditions for a given solution are 10° C. or less below the $T_m$, 5° C. or less below the $T_m$, 3° C. or less below the $T_m$, 1° C. below the $T_m$, or at about the $T_m$ of the subject hybridized compliments. The $T_m$ of a DNA-DNA duplex can be estimated using the following equation:

$$T_m(°C.)=81.5°C.+16.6(\log_{10}M)+0.41(\%G+C)-0.72(\%f)-500/n,$$

where M is the molarity of the monovalent cations (usually Na+), (% G+C) is the percentage of guanosine (G) and cystosine (C) nucleotides, (% f) is the percentage of formamide and n is the number of nucleotide bases (i.e., length) of the hybrid. See, Rapley and Walker, supra. The $T_m$ of an RNA-DNA duplex can be estimated as follows:

$$T_m(°C.)=79.8°C.+18.5(\log_{10}M)+0.58(\%G+C)-11.8(\%G+C)^2-0.56(\%f)-820/n,$$

where M is the molarity of the monovalent cations (usually Na+), (% G+C) is the percentage of guanosine (G) and cystosine (C) nucleotides, (% f) is the percentage of formamide and n is the number of nucleotide bases (i.e., length) of the hybrid. Id. Equations 1 and 2 are typically accurate only for hybrid duplexes longer than about 100-200 nucleotides. Id. The Tm of nucleic acid sequences shorter than 50 nucleotides can be calculated as follows:

$$T_m(°C.)=4(G+C)+2(A+T),$$

where A (adenine), C, T (thymine), and G are the numbers of the corresponding nucleotides.

In certain embodiments of the invention all of the hybridizations of the amplification complex are designed to have melting temperatures within about 5° C. of each other. In other cases, all the melting temperatures are designed to be within about 3° or about 1° C. of each other. In other embodiments, the melting temperatures of hybridizations in the complexes are designed to have higher melting temperatures for hybridizations initiated early in am amplification and lower melting temperatures for hybridizations initiated later in the amplification process (e.g., with stringent washes between the hybridizations).

Blocking probes can optionally be hybridized to the nucleic acids of interest, e.g., in bDNA amplifications to reduce background in the assay. For a given nucleic acid of interest, the corresponding label extenders, optional capture extenders, and optional blocking probes are preferably complementary to physically distinct, non-overlapping sequences in the nucleic acid of interest, which are preferably, but not necessarily, contiguous. It can be desirable to include blocking probes in bDNA amplifications, which are complimentary to all target nucleic acid sequences not hybridized to other components of the amplification system. The $T_m$s of the capture extender-nucleic acid, label extender-nucleic acid, and blocking probe-nucleic acid complexes are preferably greater than the temperature at which the capture extenders, label extenders, and/or blocking probes are hybridized to the nucleic acid, e.g., by 5° C. or 10° C. or preferably by 15° C. or more, such that these complexes are stable at that temperature. Potential CE and LE sequences (e.g., potential sequences C-3 and L-1) are optionally examined for possible interactions with non-corresponding nucleic acids of interest, LEs or CEs, the preamplifier, the amplification multimer, the label probe, and/or any relevant genomic sequences, for example; sequences expected to cross-hybridize with undesired nucleic acids are typically not selected for use in the CEs or LEs. See, e.g., Player et al. (2001) "Single-copy gene detection using branched DNA (bDNA) in situ hybridization", J. Histochem. Cytochem. 49:603-611 and U.S. patent application 60/680,976. Examination can be, e.g., visual (e.g., visual examination for complementarity), computational (e.g., computation and comparison of binding free energies), and/or experimental (e.g., cross-hybridization experiments). Capture probe sequences are preferably similarly examined, to ensure that the polynucleotide sequence C-1 complementary to a particular capture probe's sequence C-2 is not expected to cross-hybridize with any of the other capture probes that are to be associated with other subsets of particles or selected positions on the support.

Hybridized nucleic acid duplexes align antiparallel. In figures, where one nucleic acid strand is displayed in one orientation (e.g., 5' to 3' left to right), the complimentary strand will be in the opposite orientation (e.g., 3' to 5'). In complexes of the invention, components in serial association are designed to alternate between these orientations. For example, where a capture probe is attached to a solid support from a 3' end with the 5' end extending away from the solid support, complimentary capture extenders are typically designed to provide the complimentary sequence on the 5' end, thus leaving the capture extender 3' end free of the solid support surface to capture a target nucleic acid. Similarly, if a label extender is designed with a complimentary sequence at the 5' end intended to hybridize with a captured nucleic acid of interest (leaving the 3' LE end free), an amplification multimer compliment strand will typically be designed with a 3' end sequence free to specifically hybridize to the free 3' end of the label extender.

The various hybridization and capture steps can be performed simultaneously or sequentially, in any convenient order. For example, in embodiments in which capture extenders are employed, each nucleic acid of interest can be hybridized simultaneously with its corresponding label extenders and its corresponding capture extenders in solution, and then the capture extenders can be hybridized with capture probes associated with the solid support. Materials not captured on the support are preferably removed, e.g., by washing the support, and then the label probe system is hybridized to the label extenders.

Washing Solid Supports

At any of various steps, materials not captured on the solid support are optionally separated from the support by washing. For example, after the capture extenders, nucleic acids, label extenders, blocking probes, and support-bound capture probes are hybridized, the support is optionally washed to remove unbound nucleic acids and probes; after the label extenders and amplification multimer are hybridized, the support is optionally washed to remove unbound amplification multimer; and/or after the label probes are hybridized to the amplification multimer, the support is optionally washed to remove unbound label probe prior to detection of the label. The support is optionally washed at the end of the first amplification to remove unbound amplification oligomers.

After hybridization steps in the methods, unhybridized nucleic acid material can be removed by a series of washes, the stringency of which can be adjusted depending upon the desired results. Low stringency washing conditions (e.g., using higher salt and lower temperature) can increase sensitivity, but can produce nonspecific hybridization signals and high background signals. Higher stringency conditions (e.g., using lower salt and a higher temperature that is closer to the hybridization temperature) lowers the background signal, typically with only the specific signal remaining. See, Rapley, R. and Walker, J. M. eds., *Molecular Biomethods Handbook* (Humana Press, Inc. 1998), which is incorporated herein by reference in its entirety for all purposes. "Stringent hybridization wash conditions" in the context of the amplification methods, are sequence dependent. An extensive guide to the hybridization of nucleic acids is found in Tijssen (1993), supra, and in Hames and Higgins 1 and Hames and Higgins 2, supra.

Transferring Amplification Oligomers to a Second Amplification

At the end of the first amplification, the amplification oligomers accumulated on the first solid support can be melted back into a solution and, optionally, transferred physically to a new location for the second amplification or nucleic acid assay.

At the end of a typical first amplification, a capture probe on a solid support is hybridized to a capture extender, which is hybridized to the target nucleic acid, which is hybridized to one or more label extenders, which are hybridized to amplifier multimers, which are hybridized to a large number of amplification oligomers. See, e.g., FIG. 3A. Any excess amplification components or sample materials are washed away from the solution surrounding the bound materials on the solid support. Ideally, melting conditions can be provided that substantially melt the amplification oligomers from the amplification multimers while the other noted hybridizations do not melt. This could be accomplished by providing a lower $T_m$ for the amplification oligomer hybridization than for the other hybridizations of the first amplification. With the amplification oligomer melting at a lower temperature from the amplification oligomer, the amplification oligomer could be melted into solution at a high purity. Highly pure amplification oligomer can under some circumstances have advantages of lower background and higher sensitivity in the second amplification. Alternately, the melting solution and temperature can melt all hybridizations of the first amplification; any background issues resolvable by intelligent choice of second amplification components and component concentrations. For example, melting temperatures of system components can be manipulated by selection of complimentary sequence length, sequence (e.g., GC %), use of unnatural base analogs, employment of locked nucleic acids (LNA), etc.

Solutions for melting amplification oligomers from the first amplification can provide conditions (e.g., low salt and high temperature) that can melt hybridizations of the amplification oligomer. Optionally, the melting solution can provide conditions, e.g., buffers, salts and components, appropriate to the second amplification reaction. For example, where the second amplification is a bDNA amplification, the melting solution can include the capture extenders, label extenders, amplification multimers and buffer solutions of the second amplification system. In another example, where the second amplification is a PCR reaction, the melting solution can include, e.g., taq polymerase, PCR primers, nucleotide triphosphates, and/or other components of the PCR reaction.

The solution of amplification oligomer melted from the solid support of the first amplification can be transferred by any appropriate means known in the art. For example, the solution of unbound amplification oligomers can be aspirated with pipettes and manually or robotically transferred to the surface or chamber of the second amplification. The solution of amplification oligomers can be pumped through a conduit of from the first amplification to the location of the second amplification.

In certain embodiments, the amplification oligomer accumulated in the first amplification does not have to be transferred to a new location (e.g., chamber of surface) in order to carry out the second amplification. The second amplification can be carried out, for example, by adding components of a second bDNA assay or an enzymatic amplification to the first amplification product, e.g., in the presence of the first solid support.

For example, after the excess components of the first amplification have been washed away, the hybridized components can be melted into the reaction solution of the second amplification containing, e.g., an excess of second capture extenders, second label extenders second amplification multimers and label probes. The capture extenders can have sequences complimentary to the same capture probes of the first amplification but instead of the sequence complimentary to the target nucleic acid of interest from the sample, the second capture extender can have a sequence complimentary to sequences of the amplification oligomer. Alternately, the second capture extenders can have sequences complimentary to the amplification oligomers and to a second set of capture probes on the first solid support. The second label extenders can have sequences complimentary to sequences on the amplification oligomers and to the second amplification multimer, which has many sequences complimentary to label probes. The second amplification can be driven with a large excess of second amplification components. Judicious use of blocker probes can minimize interactions of the amplification oligomers with residual components of the first amplification.

In another example, a second amplification can take place without transfer of the accumulated and melted amplification oligomers by adding components a polymerase chain reaction to the amplification oligomers. For example, the solid support of the first amplification can be in an Eppendorf tube that fits in a heat block of a thermocycler used for running PCR reactions. After the washing step to remove inbound components of the first amplification, the accumulated amplification oligomer can be melted into a solution containing all components of a PCR reaction. For example, the melting solution can include a PCR primer pair—a first primer complimentary to the amplification oligomer and a second primer having, e.g., the same sequence as a portion of the amplification oligomer at some point 5' along the oligomer from the compliment of the first primer. A polymerase chain reaction using these primers would replicate multiple copies of both strands between and including the primers.

Detecting Amplification Oligomers

Amplification oligomers accumulated by binding to the first solid support in the presence of the target nucleic acid of interest can be detected by various means to confirm the presence of the target in the sample. In preferred embodiments of the methods, the amplification oligomer is detected in or after a second non-enzymatic or enzymatic amplification.

In many embodiments of the invention, the amplification oligomers can be detected without further enzymatic or non-enzymatic amplification steps. For example, the amplification oligomers can be detected by 280 nm absorbance, fluorometry in the presence of ethidium bromide, polyacrylamide gel electrophoresis, Southern blotting, northern blotting, and the like.

In preferred embodiments, the amplification oligomer is detected indirectly in a nucleic acid assay. For example, the presence of the amplification oligomer can be confirmed by amplification of the amplification oligomer in a second amplification providing another nucleic acid as the detectable amplification product. The amplification oligomer amplification product of the first amplification can be detected (and optionally quantitated) in a second amplification, such as, e.g., a PCR amplification, a TaqMan assay, a ligase chain reaction, a branched DNA assay providing a labeled probe amplification product, and the like. A second bDNA amplification providing another amplification oligomer can be run before detection of the second amplification oligomer directly or by an enzymatic or non-enzymatic amplification assay.

In preferred embodiments of the methods, the amplification oligomer does not include a label and is not detected by direct detection of a label on the oligomer (e.g., the amplification oligomer is not a label probe). In preferred methods of the invention, the amplification oligomer is not detected indirectly as the product of an enzymatically catalyzed reaction (e.g., the presence of amplification oligomer is not detected through the detection of an enzymatic replication product (e.g., PCR product) of the amplification oligomer.

In a more preferred embodiment of detecting the amplification oligomer product of a first amplification, the amplification oligomer is detected in a second branched DNA assay. For example, the first solid support binding the amplification oligomer is washed and then melted into a melting solution of appropriate stringency for a second amplification. The melting solution can include components of the branched DNA second amplification, such as, e.g., capture extenders, blocking probes, and a label system (e.g., label extenders, preamplifiers, amplifiers, and/or label probes). It is preferred that capture extenders and label extenders be in substantial excess over residual amplification multimers carried over from the first amplification. The solution containing the amplification oligomers can be transferred to a second solid support comprising capture probes with sequences complimentary to a sequence on the capture extenders. The transferred solution and solid support can be brought to a temperature above the melting temperatures of the amplification system components, then brought to a stringent hybridization temperature. Many of the hybridization interactions can take place in solution between the soluble components, but ultimately the amplification complex will be captured at the solid support by hybridization of the capture extender to the solid support capture probes. The solid support can be washed with one or more wash solutions, under stringent conditions. The presence of the amplification oligomer (and associated target nucleic acid in interest in the sample) can be detected by detection of bound, e.g., fluorescent label probes.

The methods can optionally be used to quantitate the amounts of the nucleic acids of interest present in the sample. For example, in one class of embodiments, an intensity of a signal from the label is measured and correlated (e.g., through a standard formula determined through regression analysis) with a quantity of the corresponding nucleic acid of interest present. The standard formula can then be used to calculate an unknown amount of nucleic acid in a sample based on the output signal intensity for that sample.

Amplification Oligomers

Amplification oligomers can be the output amplification product of a first amplification and the input target for a second amplification. In a typical embodiment, the amplification oligomer is a polynucleotide with a sequence complimentary to multiple repeat sequences of an amplification multimer and a sequence complimentary to a root sequence of a label system. In a more preferred embodiment, the amplification oligomer would also include a sequence complimentary to a capture polynucleotide sequence. In alternate embodiments, amplification oligomers comprise a sequence complimentary to multiple repeat sequences of an amplification multimer, a polymerase primer sequence, and a sequence complimentary to a polymerase primer. Other embodiments of amplification oligomers include a sequence complimentary to multiple repeat sequences of an amplification multimer and one or more sequences functionally interacting with an amplification system to provide a detectable amplification product.

In a preferred embodiment, an amplification oligomer is a polynucleotide with a sequence complimentary to the amplification multimer of a first bDNA amplification, and compliments to label components and (optionally) capture components of a second bDNA amplification. In a more preferred embodiment, the amplification oligomer comprises sequences complimentary to the multiple M-2 sequences of the amplification multimer of a first amplification and sequences complimentary to either M-1 sequences of the amplification multimer or L-2 sequences of the label extender of the second amplification. In most preferred embodiments, the amplification oligomer also comprises sequences complimentary to C-2 or C-3 sequences of second amplification capture components.

In an aspect of the invention, the complimentary sequences of the amplification oligomer have lengths enhancing hybridization reaction kinetics, minimizing stearic interference with desired intermolecular interactions, and providing melting temperatures compatible with overall system requirements. In embodiments described above wherein both amplification steps are bDNA amplifications, it is preferred that the amplification oligomer sequences complimentary to the M-2 sequences range in length from about 20 to about 80 nucleotides, from about 30 to about 70 nucleotides, or from about 40 to about 60 nucleotides. It is preferred the amplification oligomer sequences complimentary to the M-1 or L-2 sequences range in length from about 15 to 50 nucleotides, from about 20 to 40 nucleotides, from 25 to 30 nucleotides, or about 28 nucleotides. It is preferred the amplification oligomer sequences complimentary to the C-2 or C-3 sequences range in length from about 15 to 80 nucleotides, from about 20 to 60 nucleotides, from 25 to 50 nucleotides, or about 40 nucleotides. In certain cases, the amplification oligomer sequences complimentary to the M-1 or L-2 sequences, or the amplification oligomer sequences complimentary to the C-2 or C-3 sequences include two or more repeat or redundant sequences so that, e.g., label or capture systems of the second amplification can readily employ cooperative hybridization features.

The complimentary sequences of the amplification oligomers can be in any order along the polynucleotide. It is generally preferred that the amplification oligomer sequences complimentary to the M-2 sequences of the first amplification be between the sequences complimentary to the C-2 or C-3 (capture) sequences and sequences complimentary to the M-1 or L-2 (label) sequences. This arrangement can allow better hybridization kinetics and reduce stearic hindrance, e.g., between the solid support components and label system. In more preferred embodiments, the amplification oligomer has sequences configured to provide cooperative hybridization. For example, the amplification oligomer can have multiple sequences complimentary to multiple capture or label system sequences. In embodiments with cooperative hybridization, the amplification oligomer sequences can be complimentary in the order: capture-label-M2-label-capture, label-capture-M2-capture-label, label-capture-M2-label-capture, label-label-M2-capture-capture, M2-label-label-capture-capture, M2-capture-label-label-capture, M2-capture-label-label-capture-label-capture, and the like. The order can run 5' to 3' or 3' to 5', e.g., depending on the orientation of associated compliments.

In an aspect of the invention, two or more different amplification oligomers are provided as amplification products of the first amplification. In a preferred embodiment, the two or more different amplification oligomers have sequences complimentary to different amplification multimer M-2 sequences of the first amplification and/or sequences complimentary to different capture C-2 or C-3 sequences of the second amplification. Optionally, the two or more different amplification oligomers have sequences complimentary to different label system L-2 or M1 sequences. The use of different amplification oligomer sequences, e.g., in association with analysis of a single sample can allow multiplexing that can be deconvoluted according to final signal character and/or final signal locations, as discussed below. For example, amplification oligomers having different capture compliments can be directed to capture on solid supports at different physical locations. Optionally, amplification oligomers with different label compliments can associate with, e.g., labels emitting different fluorescent wavelengths. Optionally, amplification oligomers with different M-2 compliments can be accumulated at different locations (e.g., different beads) in a first amplification so they can be detected in a standard second amplification separate from other amplification oligomers accumulated elsewhere in the first amplification.

In another aspect, the melting temperatures of the amplification oligomer sequences hybridized to their compliments is considered to provide useful structure/function relationships between components of two-stage amplifications. For example, the sequence complimentary to M-2 sequences of the first amplification can have a $T_m$ within 10° C., 5° C. or 2° C. of other hybridizations (e.g., capture probe/capture extender, capture extender/target. target/label extender, label extender/amplification multimer) of the first amplification. Provision of similar $T_m$s can allow more stringent hybridizations and washes, e.g., without excessive background or signal loss. Optionally, the sequence complimentary to M-2 sequences of the first amplification can have a $T_m$ significantly lower than for the other hybridizations, so that, e.g., the accumulated amplification oligomer can be harvested during the melting step without also releasing other amplification components from the solid support. In such a system, one should consider hybridizing all the target and bDNA amplification components without the amplification oligomer at a higher stringency temperature, than hybridizing an excess of amplification oligomer at a lower temperature before the wash. In another aspect, it can be preferred that the $T_m$ for the M-2 compliment of the first amplification be lower than the $T_m$ for the capture compliment or label compliment, e.g., so that residual amplification multimers from the first amplification are less likely to interfere with a second bDNA amplification.

In other aspects of the invention, the amplification oligomers can include a compliment to the amplification multimer of a bDNA amplification, a compliment to the first primer of a PCR primer pair, and a sequence substantially the same as the sequence of the second primer of the PCR primer pair. This amplifier oligomer configuration allows a first amplification of a target nucleic acid of interest from a complex sample that might have enzyme inhibiting materials to produce a product more compatible with a second amplification system. For example, the amplified material can be separated from any enzyme inhibitors of the sample, e.g., in the wash of the first amplification so provides a consistent substrate for the PCR second amplification. Amplification oligomers for a two-stage amplification of bDNA to PCR can have, e.g., the compliment to the M-2 sequence between the primer sequence and primer compliment. The PCR can replicate the primers and sequences in between in a geometric fashion, as is notoriously well known in the art. The product of the PCR can be detected directly or indirectly by enzymatic or non-enzymatic methods. The amplification oligomers of the bDNA/PCR two-stage amplification can include compliments of capture sequences (e.g., between the PCR primer pair sites) to render the PCR product directable to identifiable physical locations.

In an aspect of the invention, amplification oligomers typically do not comprise a label. The amplification oligomers can be accumulated in amounts that are directly detectable without the need for constitutive labels. Further, the amplification oligomers are usually not intended to be detected, identified or quantitated directly, but are intended to act as input target material for a second amplification that provides a detectable labeled product output.

Multiplexing Two-Stage Amplification Signals

Amplification oligomers of the invention are not only a key to two-stage amplifications that substantially enhance the sensitivity of nucleic acid assays, but can also provide ways to perform and read two nucleic acid assays at once for the same sample. In a first bDNA amplification, the hybridization between the target nucleic acid of interest and the label system can be specific and unique. That is, a first nucleic acid of interest can hybridize, e.g., through L-2 or M-1 sequences, with a first amplification multimer, which can specifically accumulate a first amplification oligomer. At the same time, in the same sample, a second nucleic acid of interest can hybridize, through, e.g., different L-2 or M-1 sequences, with a second amplification multimer, which can specifically accumulate a different second amplification oligomer. If the first and second amplification oligomers bind to different solid support locations, or hybridize to different labeling systems e.g., in a second amplification, the presence of the first and second nucleic acids of interest in the sample can be separately detected at the separate locations and/or as distinguishable label system signals.

Amplification oligomers can allow the results of two or more nucleic acid analyses to be read at the same time at different locations. Identity information for a target nucleic acid can be retained through a chain of specific hybridization. For example, identity of a particular nucleic acid of interest can be retained through specific hybridizations from the nucleic acid to a label extender to an amplification multimer to a to a particular amplification oligomer. The amplification oligomer can have a sequence complimentary to the capture system of a specific solid support so that amplification oligomer detected at that solid support can be read as confirming the presence of the target nucleic acid in the sample. The presence of a second target nucleic acid in the same sample can be read at a different solid support location determined by a specific combination of label extenders, amplification multimers, amplification oligomers and solid support capture elements associated with the second target nucleic acid.

In an exemplary embodiment of target amplifications multiplexed to separate solid support locations, a first solid support is provided to allow capture of all nucleic acids of interest that may or may not be present in a sample. This solid support can, e.g., non-specifically bind all nucleic acids or, in a preferred embodiment, include capture probes with a range of capture extenders complimentary to the whole range of nucleic acids of interest. Captured nucleic acids of interest can then be specifically hybridized (directly or through any number of specific extenders) to an array of amplification multipliers. Each of the amplification multimer array members can be specifically hybridized to particular amplification oligomers each having sequences complimentary to specific capture elements (e.g., capture probes or capture extenders) bound to defined regions of a second solid support. In a multiplexed two-stage amplification, the array of first amplification multimers is specifically hybridized to their specific target nucleic acids on the first solid support. An array of amplification oligomers is provided to specifically hybridize and accumulate on their complimentary amplification multimers. When the first solid support is stringently washed, amplification multimers and accumulated amplification oligomers not bound to the solid support through the presence of their target nucleic acid are removed. A melting solution at elevated temperatures can then releases bound amplification oligomers from the first solid support into the solution. One or more second solid supports can be contacted with the solution of amplification oligomers. In preferred embodiments, the solid support surface includes a matrix of locations (e.g., column/row positions) that each have different specific capture sequences (e.g., capture probe C-2 or capture extender C-3 sequences) capable of hybridizing to one member of the amplification oligomer array, but not to other members. On contact, under stringent hybridization conditions, the amplification oligomers, previously bound to the first solid support through association with their nucleic acid of interest, segregate to their designated matrix location through hybridization to their specific capture sequence. At this point in the matrixed two-stage amplification, all the bound amplification oligomers can be detected through a general non-specific detection—the identity information for the target nucleic acids has been retained through the previous steps and can now be determined as the presence of amplification oligomers at the specific locations. The amplification oligomers at each location can all have the same sequence complimentary to a general use labeling system. For example, all the amplification oligomers can have a sequence complimentary to the same amplification multimer M-1 sequence for binding of the amplification multimer and multiple associated label probes. Detection of label probe signals at specific locations of the second solid support can be deconvoluted to specifically confirm the presence of one or two or more different nucleic acids of interest in the original sample.

In other embodiments of deconvolution by second solid support location, the second solid support can be a conduit or beads and contact of the amplification oligomer solution to the multiple locations can be in series or in parallel. For example, the melted solution of amplification oligomers can be transferred to a chamber containing two or more beads, each bead having a different detectable identification signal and having capture systems with different specificity on the surface. Two or more different amplification oligomers can be captured on different beads. After contact with a label system, a label probe signal from a bead with a particular identification signal can confirm the presence of a particular nucleic acid of interest in the original sample. Alternately, the beads can be lined up in a series and be contacted sequentially with the melted solution of amplification oligomers for specific capture. In another embodiment, the surface of a conduit could be provided with a linear array of different capture components to selectively hybridize and capture each of the different amplification oligomers at a different location along the conduit. After exposure to a label system, signals at particular locations along the conduit can confirm the presence of particular nucleic acids of interest in the original sample.

In another embodiment of matrixing with bead solid supports, the first solid supports are an array of beads having different capture systems and the identity of the captured target nucleic acids is deconvoluted by sorting the beads. For example, in a first amplification the putative target nucleic acids are contacted to an array of beads each having a unique identification signal, and each of which has a different capture system with different capture specificity. Any nucleic acids of interest present in the sample will hybridize and become specifically bound to their corresponding bead. All the beads of the array can optionally be contacted with the same general use system of amplification multimers and amplification oligomers. Before, during or after contact with the amplification multimers, the beads can be sorted to separate locations according to their identification signal, e.g., using a particle sorter. The beads can be washed, typically before or during the bead sorting. The second amplification (e.g., of the amplification oligomers bound to the beads) and detection can take place at the location resulting from the sorting process. Detection of second amplification label probe signals at the location or in association with the identity signals of various beads can confirm the presence of one, or two or more, nucleic acids of interest in the original sample.

In still another example of multiplexed two-stage amplification methods employing amplification oligomers, each different amplification oligomer has a unique label system compliment so that different amplification oligomers at the same location can be separately identified and quantitated. In an exemplary embodiment, two or more target nucleic acids of interest are captured on a first solid support and amplified to accumulate amplification oligomers specific to those putative target nucleic acids actually present, as previously discussed above. The amplification oligomers associated with each target can each have sequences complimentary to different label systems, but can all include sequences complimentary to the same capture system. After washing the solid support, the accumulated amplification oligomers can be transferred and be captured (specifically or non-specifically) on a second solid support. The labeling system of the second amplification includes an array of amplification multimers, each member of the array accumulating different label probes with distinguishable signals. Different combinations of signals in the second amplification can thereby identify different combinations of target nucleic acids that were present in the initial sample. This multiplexed two-stage amplification can provide signals that can be deconvoluted from the same location at the same time, e.g., by reading multiple distinguishable signals. In an optional aspect, the amplification oligomers from the first amplification can be captured on the second solid support through non-specific chemical interactions. In an optional aspect, after washing, the accumulated amplification oligomers can be melted and specifically or non-specifically captured on the same solid support for the second amplification. In an optional aspect, the washed accumulated amplification oligomers, still hybridized to first amplification multimers, can take part in the second amplification, e.g., by contacting with the label system of the second amplification.

In another aspect of two-stage amplifications, the amplification oligomers associated with different target nucleic acids of interest can each have compliments to different capture systems and compliments to different label systems. In this configuration, the identity of each nucleic acid can be associated with a particular signal at a particular location. For example, a sample containing four different target nucleic acids of interest can be captured on a first solid support (specifically or non-specifically). The captured nucleic acids can be contacted with four different amplification multimers that each specifically hybridize with only one of the target nucleic acids. The amplification multimer "A" hybridizes to the first target nucleic acid and to a first amplification oligomer, which comprises a compliment to a first label system having a green signal and a compliment to the capture system at location (1,1) of a second solid support. The amplification multimer "B" hybridizes to the second target nucleic acid and to a second amplification oligomer, which comprises a compliment to a second label system having a red signal and a compliment to the capture system at location (1,2) of the second solid support. The amplification multimer "C" hybridizes to the third target nucleic acid and to a third amplification oligomer, which comprises a compliment to a third label system having a yellow signal and a compliment to the capture system at location (1,2) of the second solid support. The amplification multimer "D" hybridizes to the fourth target nucleic acid and to a fourth amplification oligomer, which comprises a compliment to a fourth label system having a yellow signal and a compliment to the capture system at location (1,1) of the second solid support. In the first amplification of the sample, the first, second, third and fourth amplification oligomers are accumulated on the first, second, third and fourth amplification multimers, respectively. After washing and melting, the amplification oligomers are transferred in the same solution to the second solid support where they are captured at locations (1,1), (1,2), (1,2) and (1,1), respectively. In a second amplification comprising the first (green), second (red) and third (yellow) amplification systems, a pattern of locations and signals can be deconvoluted to identify the nucleic acids of interest in the original sample. That is, the presence of green and yellow signals at location (1,1) would be identify the presence of both the first nucleic acid and fourth nucleic acid in the sample. The presence of red and yellow signals at location (1,2) would be identify the presence of both the second nucleic acid and third nucleic acid in the sample. Thus, from one sample four nucleic acids were identified at two locations at the same time. This exemplary embodiment is not intended to be limiting and one skilled in the art will appreciate from this description that, depending on the number of locations and signals employed, the number of nucleic acids identifiable by this two-stage double multiplexed technique can become quite large. For example, about $10^4$ different nucleic acids could be identified from the same sample at the same time (e.g., using CCD detection), assuming amplification oligomers in concert with a second amplification having combination of 11 different label signals and a second solid support with locations in a grid of 30 rows and 30 columns. Alternately, the detection could be sequential and/or the solid support could include any number of beads, e.g., with identity signals.

For an assay to achieve high specificity and sensitivity, it preferably has a low background, resulting, e.g., from minimal cross-hybridization. Such low background and minimal cross-hybridization are typically substantially more difficult to achieve in a multiplex assay than a single-plex assay, because the number of potential nonspecific interactions are greatly increased in a multiplex assay due to the increased number of probes used in the assay (e.g., the greater number of capture extenders and label extenders. In preferred embodiments of multiplexed two-stage amplifications, cooperative hybridizations are employed in the capture and/or labeling interactions. For example, an amplification oligomer in a second amplification can be designed to include two different sequences complimentary to two different capture (e.g., C-2 or C-3) sequences. Hybridization stringency can be such that capture by only one sequence (or capture by two sequences with substantial mis-matches) does not take place. With regard to label systems, the amplification oligomer in a second amplification can be designed to include two different sequences complimentary to two different label system (e.g., L-2 or M-1) sequences, e.g., for multiple simultaneous LE-label probe system component interactions. This reduction in background through minimization of unintended cross-hybridization events thus facilitates multiplex detection of the nucleic acids of interest.

Two-Stage Amplification Systems

Amplification systems of the invention include components useful in the practice of methods of the invention. Typical two-stage amplification systems include one or more first solid supports functioning to capture nucleic acids of interest, one or more first amplification multimers, a second solid support functioning to capture an amplification oligomer, a label system, and one or more amplification oligomers complimentary to the first amplification multimer and complimentary to a sequence of the label system. The systems can further include hardware and information systems, e.g., to facilitate solution handling, process condition control, signal detection, information storage, and/or the like.

In one aspect, the invention includes, e.g., systems used to practice the methods herein and/or systems comprising the compositions described herein. The system can include, e.g., a fluid and/or bead handling element, a fluid and/or bead containing element, a laser for exciting a fluorescent label and/or fluorescent beads, a detector for detecting light emissions from a chemiluminescent reaction or fluorescent emissions from a fluorescent label and/or fluorescent beads, and/or a robotic element that moves other components of the system from place to place as needed (e.g., a multiwell plate handling element). For example, in one class of embodiments, a composition of the invention is contained in a flow cytometer, a Luminex 100™ or HTS™ instrument, a microplate reader, a microarray reader, a luminometer, a colorimeter, or like instrument.

The system can optionally include a computer. The computer can include appropriate software for receiving user instructions, either in the form of user input into a set of parameter fields, e.g., in a GUI, or in the form of preprogrammed instructions, e.g., preprogrammed for a variety of different specific operations. The software optionally converts these instructions to appropriate language for controlling the operation of components of the system (e.g., for controlling a fluid handling element, robotic element and/or laser). The computer can also receive data from other components of the system, e.g., from a detector, and can interpret the data, provide it to a user in a human readable format, or use that data to initiate further operations, in accordance with any programming by the user.

Figure 4:
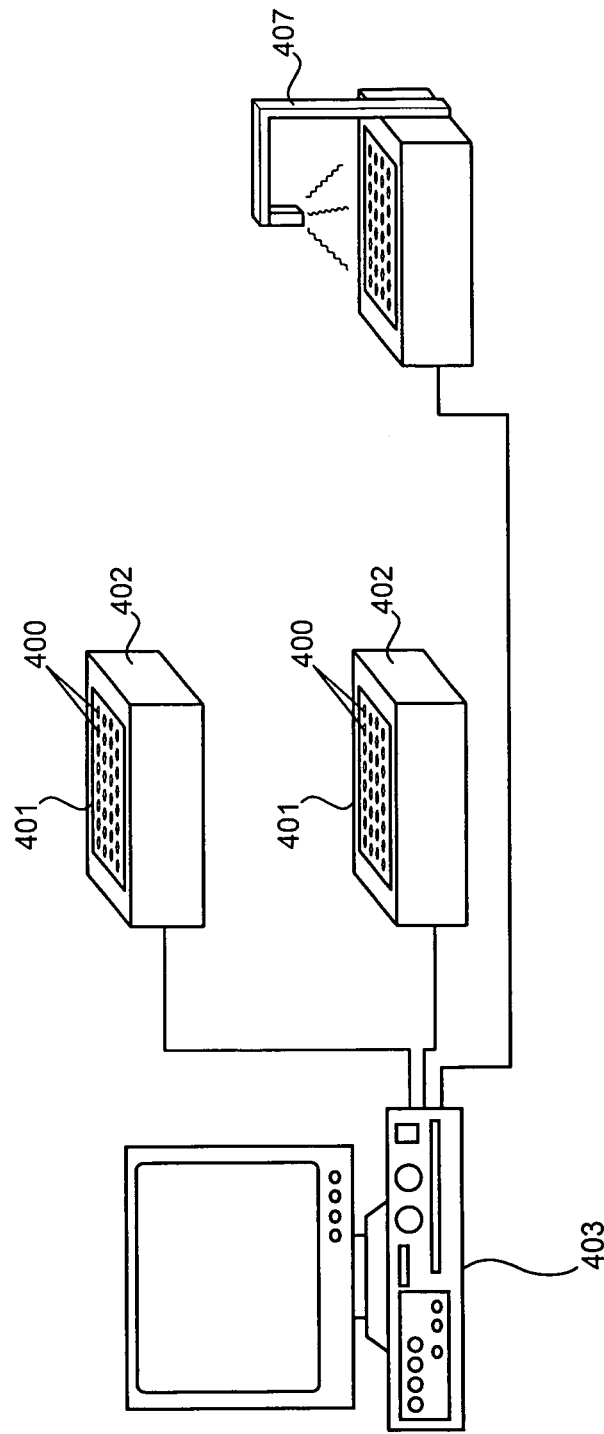
FIG. 4 is a schematic diagram of exemplary two-stage amplification system hardware components.

In an exemplary embodiment of the systems, wells 400 of a first multi-well plate 401 have a surface presenting a capture probe and holding a first solution containing a combination of first capture extenders, blocking probes, first label extenders, first amplification multimers and amplification oligomers. The multiwell plate is in contact with a heat plate 402 temperature controllable through a computer system 403, as shown in FIG. 4. The system includes a second multiwell plate 404 with second capture probes on the well surfaces 405, and a second solution containing a combination of second capture extenders, second label extenders, second amplification multimers and label probes.

The system components can function together in a two-stage amplification, for example, as follows: 1) a sample containing a nucleic acid of interest is added to the first solution; 2) the computer 403 commands the heating plate 402 to provide a melting temperature (e.g., 95° C.) in the wells 400 to melt any hybridized nucleic acids to single strand form; 3) the computer 403 commands the heating plate 402 to provide a stringent hybridization temperature to the solution in the wells 400; 4) components of the first amplification specifically hybridize with each other to ultimately accumulate a large number of amplification oligomers at the well surface, as described herein (e.g., in a complex of capture probes to capture extenders to target nucleic acid to label extenders to amplification multimers to amplification oligomers); 5) the first solution, with residual components, is removed (e.g., by manual or robotic pipetting); 6) the well is washed, e.g., by manual or robotic introduction and removal of a wash solutions; 7) the second amplification solution is added to the well and the computer 403 commands the heating plate 402 to provide a melting temperature to melt the accumulated amplification oligomers from the well surface into the solution; 8) the amplification oligomers, now in the second amplification solution, are transferred to a well of the second multiwell plate 404 (held on the heating plate or another heating plate 406); 9) the computer 403 commands the heating plate 406 to transition from the melting temperature to a stringent hybridization temperature; 10) components of the second amplification specifically hybridize to each other in a complex to ultimately accumulate a large number of label probes at the well surfaces 405, as described herein (e.g., a complex of capture probes to capture extenders to amplification oligomers to label extenders to amplification multimers to label probes); 11) the second solution, with residual components, is removed; 12) the well is washed; 13) the presence and amount of detectable signal from labeled probes in the well is detected by a detector system 407; and 14) the detector system 407 transmits signal detection data to the computer system for storage and evaluation.

First Amplification Systems to Accumulate Amplification Oligomers

In a first amplification, as shown in FIG. 2A, a sample (e.g., conditioned media or lysed cells) to be analyzed by the system includes a target nucleic acid 214. The target nucleic acid 214 is captured by first capture probe 204 on solid support 201 (e.g., a well of a microtiter plate) through set 211 of synthetic oligonucleotide capture extenders. Each capture extender has a first polynucleotide sequence C-3 (252) that can stringently hybridize to the target nucleic acid and second polynucleotide sequence C-1 (251) that can stringently hybridize to the capture probe through sequence C-2 (250) of the capture probe. Typically, two or more capture extenders are used; optionally, one capture extender can be used to capture a target. Each label extender in label extenders set 221 hybridizes to a different sequence on the target nucleic acid, through sequence L-1 (254) that is complementary to the target nucleic acid, and to sequence M-1 (257) on amplification multimer (241), through sequence L-2 (255). Blocking probes (224), which hybridize to sequences in the target nucleic acid not bound by either capture extenders or label extenders, are often used in bDNA assays to reduce non-specific target probe binding. A probe set for a given target nucleic acid thus consists of capture extenders, label extenders, and optional blocking probes for the target nucleic acid. The capture extenders, label extenders, and optional blocking probes are complementary to non-overlapping sequences in the target nucleic acid, and are typically, but not necessarily, contiguous. In this example, a single blocking probe is used; typically, an array of different blocking probes is used in an optimized bDNA assay.

Signal amplification can begin with the binding of the label extenders to the target nucleic acid. The amplification multimer is then hybridized to the label extenders. The amplification multimer has multiple copies of sequence M-2 (258) that is complementary to amplification multimer 241 (it is worth noting that the amplification multimer is typically, but not necessarily, a branched-chain nucleic acid; for example, the amplification multimer can include a branched, forked, or comb-like nucleic acid or a linear nucleic acid). Note the amplification of the single initial target nucleic acid 214 captured to, e.g., eighteen amplification oligomers 242 accumulated on the first amplification multimers.

Second Amplification Systems to Accumulate Label Probes

After removal of the first solution and washing the solid support 201, the accumulated amplification oligomers 242 can be melted from the first amplification multimers 241 into a second solution containing components of the second amplification, e.g., a bDNA amplification system. The amplification oligomers 242 are captured by second capture probes 264 on second solid support 261 (e.g., a well of a microtiter plate) through second set 265 of synthetic oligonucleotide capture extenders. Each second capture extender has a first polynucleotide sequence C-3 (266) that can hybridize to the amplification oligomer 242 and second polynucleotide sequence C-1 (267) that can hybridize to the capture probe through sequence C-2 (268) in the capture probe. Typically, two or more capture extenders are used in a cooperative hybridization; optionally, one the two capture extenders can have different C-3 sequences to capture a target at different positions. Each label extender in second label extenders set 269 hybridizes to a different sequence on the target nucleic acid, through sequence L-1 (270) that is complementary to the amplification oligomer and to sequence M-1 (271) of second amplification multimer (265), through sequence L-2 (272). Blocking probes (273), which hybridize to sequences in the amplification oligomer not bound by either capture extenders or label extenders can be used to reduce, e.g., non-specific target/probe binding. A probe set for a given amplification oligomer thus consists of capture extenders, label extenders, and optional blocking probes for the amplification oligomer. The capture extenders, label extenders, and optional blocking probes are complementary to non-overlapping sequences in the amplification oligomer, and are typically, but not necessarily, contiguous.

Signal amplification can begin with the binding of the label extenders to the amplification oligomer. The amplification multimer is then hybridized to the label extenders. The amplification multimer has multiple copies of sequence M-2 (274) that is complementary to label probe 262 (it is worth noting that the second amplification multimer is typically, but not necessarily, a branched-chain nucleic acid). Label 275, for example, alkaline phosphatase, is covalently attached to each label probe. (Alternatively, the label can, e.g., be non-covalently associated with the label probes.) After removal of the second solution and one or more washing steps, labeled complexes can be detected, e.g., by the alkaline phosphatase-mediated degradation of a chemilumigenic substrate, e.g., dioxetane. Luminescence can be reported as relative light units (RLUs) on a microplate reader. The amount of chemiluminescence is proportional to the level of target nucleic acid originally present in the sample (a relationship describable with a standard function).

Solid Supports

Essentially any suitable solid support can be employed in the methods. For example, the solid support can comprise particles such as microspheres (e.g., beads), a conduit surface, or it can comprise a substantially planar and/or spatially addressable support. Different nucleic acids are optionally captured on different distinguishable subsets of particles or at different positions on a spatially addressable solid support. The nucleic acids of interest can be captured at a solid support by any of a variety of techniques, for example, by binding directly to the solid support or by binding to a moiety bound to the support, or through hybridization to another nucleic acid bound to the solid support. Preferably, the nucleic acids are captured to the solid support through hybridization with capture probes and/or capture extenders.

In some embodiments of the invention, the solid support has a planar surface and is typically rigid. The planar surface can be, e.g., the surface of a slide or an interior surface of a compartment or well. Exemplary materials for the solid support include, but are not limited to, glass, silicon, silica, quartz, plastic, polystyrene, nylon, a metal, a ceramic, and nitrocellulose. The solid support can, e.g., be a multiwell plate or a glass slide with an array of capture probes laid out in a grid pattern at selected positions.

In embodiments involving assay of a large number of samples in parallel, or multiplexed embodiments wherein many target nucleic acids are assayed from the same sample at once, the nucleic acids (e.g., sample nucleic acids of interest or associated amplification oligomers) can be captured at different positions on a non-particulate, spatially addressable solid support. Thus, in one class of embodiments, the solid support comprises two or more capture probes, wherein each capture probe is provided at a selected position on the solid support. Two or more subsets of n capture extenders can be provided, wherein n is at least two. Each subset of n capture extenders can be capable of hybridizing to one of the nucleic acids of interest, and the capture extenders in each subset can be capable of hybridizing to one of the capture probes, thereby associating each subset of n capture extenders with a selected position on the solid support. Each of the nucleic acids of interest present in the sample can be hybridized to its corresponding subset of n capture extenders and the subset of n capture extenders can be hybridized to its corresponding capture probe, thereby capturing the nucleic acid on the solid support at the selected position with which the capture extenders are associated.

Typically, in this class of embodiments, the presence or absence of the label at the selected positions on the solid support is detected after the second amplification. Since a correlation exists between a particular position on the support and a particular nucleic acid of interest, the presence of a label at a position can indicate the presence of a particular nucleic acid of interest in the sample.

In another class of embodiments, a pooled population of particles constitutes the solid support. The population comprises two or more subsets of particles, and a plurality of the particles in each subset is distinguishable (e.g., by a detectable identification signal) from a plurality of the particles in every other subset. Typically, substantially all of the particles in each subset are distinguishable from substantially all of the particles in every other subset. The particles in each subset typically have associated therewith a different capture probe.

Essentially any suitable particles can be used, e.g., particles having distinguishable characteristics and to which capture probes can be attached. For example, in one preferred class of embodiments, the particles are microspheres (e.g., small beads). The microspheres of each subset can be distinguishable from those of the other subsets, e.g., on the basis of their fluorescent emission spectrum, their diameter, or a combination thereof. For example, the microspheres of each subset can be labeled with a unique fluorescent dye or mixture of such dyes, quantum dots with distinguishable emission spectra, and/or the like. As another example, the particles of each subset can be identified by an optical barcode, unique to that subset, present on the particles.

Microspheres are preferred particles in certain embodiments described herein since they are generally stable, are widely available in a range of materials, surface chemistries and uniform sizes, and can be fluorescently dyed. Luminex Corporation ((www.) luminexcorp.com), for example, offers 100 sets of uniform diameter polystyrene microspheres. The microspheres of each set are internally labeled with a distinct ratio of two fluorophores. A flow cytometer or other suitable instrument can thus be used to classify each individual microsphere according to its predefined fluorescent emission ratio. Fluorescently-coded microsphere sets are also available from a number of other suppliers, including Radix Biosolutions ((www.) radixbiosolutions.com) and Upstate Biotechnology ((www.) upstatebiotech.com). Alternatively, BD Biosciences ((www.) bd.com) and Bangs Laboratories, Inc. ((www.) bangslabs.com) offer microsphere sets distinguishable by a combination of fluorescence and size. As another example, microspheres can be distinguished on the basis of size alone, but fewer sets of such microspheres can be multiplexed in an assay because aggregates of smaller microspheres can be difficult to distinguish from larger microspheres.

Microspheres with a variety of surface chemistries are commercially available, from the above suppliers and others (e.g., see additional suppliers listed in Kellar and Iannone (2002) "Multiplexed microsphere-based flow cytometric assays" Experimental Hematology 30:1227-1237 and Fitzgerald (2001) "Assays by the score" The Scientist 15[11]: 25). For example, microspheres with carboxyl, hydrazide or maleimide groups are available and permit covalent coupling of molecules (e.g., polynucleotide capture probes with free amine, carboxyl, aldehyde, sulfhydryl or other reactive groups) to the microspheres. As another example, microspheres with surface avidin or streptavidin are available and can bind biotinylated capture probes; similarly, microspheres coated with biotin are available for binding capture probes conjugated to avidin or streptavidin. In addition, services that couple a capture reagent of the customer's choice to microspheres are commercially available, e.g., from Radix Biosolutions ((www.) radixbiosolutions.com).

Protocols for using such commercially available microspheres (e.g., methods of covalently coupling polynucleotides to carboxylated microspheres for use as capture probes, methods of blocking reactive sites on the microsphere surface that are not occupied by the polynucleotides, methods of binding biotinylated polynucleotides to avidin-functionalized microspheres, and the like) are typically supplied with the microspheres and are readily utilized and/or adapted by one of skill In addition, coupling of reagents to microspheres is well described in the literature. For example, see Yang et al. (2001) "BADGE, Beads Array for the Detection of Gene Expression, a high-throughput diagnostic bioassay" Genome Res. 11:1888-98; Fulton et al. (1997) "Advanced multiplexed analysis with the FlowMetrix™ system" Clinical Chemistry 43:1749-1756; Jones et al. (2002) "Multiplex assay for detection of strain-specific antibodies against the two variable regions of the G protein of respiratory syncytial virus" 9:633-638; Camilla et al. (2001) "Flow cytometric microsphere-based immunoassay: Analysis of secreted cytokines in whole-blood samples from asthmatics" Clinical and Diagnostic Laboratory Immunology 8:776-784; Martins (2002) "Development of internal controls for the Luminex instrument as part of a multiplexed seven-analyte viral respiratory antibody profile" Clinical and Diagnostic Laboratory Immunology 9:41-45; Kellar and Iannone (2002) "Multiplexed microsphere-based flow cytometric assays" Experimental Hematology 30:1227-1237; Oliver et al. (1998) "Multiplexed analysis of human cytokines by use of the FlowMetrix system" Clinical Chemistry 44:2057-2060; Gordon and McDade (1997) "Multiplexed quantification of human IgG, IgA, and IgM with the FlowMetrix™ system" Clinical Chemistry 43:1799-1801; U.S. Pat. No. 5,981,180 entitled "Multiplexed analysis of clinical specimens apparatus and methods" to Chandler et al. (Nov. 9, 1999); U.S. Pat. No. 6,449,562 entitled "Multiplexed analysis of clinical specimens apparatus and methods" to Chandler et al. (Sep. 10, 2002); and references therein.

Methods of analyzing microsphere populations (e.g. methods of identifying microsphere subsets by their size and/or fluorescence characteristics, methods of using size to distinguish microsphere aggregates from single uniformly sized microspheres and eliminate aggregates from the analysis, methods of detecting the presence or absence of a fluorescent label on the microsphere subset, and the like) are also well described in the literature. See, e.g., the above references.

Suitable instruments, software, and the like for analyzing microsphere populations to distinguish subsets of microspheres and to detect the presence or absence of a label (e.g., a fluorescently labeled label probe) on each subset are commercially available. For example, flow cytometers are widely available, e.g., from Becton-Dickinson ((www.) bd.com) and Beckman Coulter ((www.) beckman.com). Luminex 100™ and Luminex HTS™ systems (which use microfluidics to align the microspheres and two lasers to excite the microspheres and the label) are available from Luminex Corporation ((www.) luminexcorp.com); the similar Bio-Plex™ Protein Array System is available from Bio-Rad Laboratories, Inc. ((www.) bio-rad.com). A confocal microplate reader suitable for microsphere and planar matrix analysis, the FMAT™ System 8100, is available from Applied Biosystems ((www.) appliedbiosystems.com).

As another example of particles that can be adapted for use in the present invention, sets of microbeads that include optical barcodes are available from CyVera Corporation ((www.) cyvera.com). The optical barcodes are holographically inscribed digital codes that diffract a laser beam incident on the particles, producing an optical signature unique for each set of microbeads.

The particles optionally have additional desirable characteristics. For example, the particles can be magnetic or paramagnetic, which provides a convenient means for separating the particles from solution, e.g., to simplify separation of the particles from any materials not bound to the particles.

Amplification Oligomers

Amplification oligomers of the systems can be essentially as described in the Amplification Oligomers section of the Methods, above. The amplification oligomers of the inventive systems typically comprise at least a sequence complimentary to a first amplification multimer (e.g., at multiple repeat sequences functioning to accumulate nucleic acids in a non-enzymatic amplification) and one or more sequences complimentary to components of a second amplification system. With these features, the amplification oligomers can function as the product of a first non-enzymatic nucleic acid amplification and as the substrate for a second enzymatic or non-enzymatic amplification.

Where the second amplification involves a bDNA system, the sequences complimentary to components of the second amplification system are typically complimentary to a second amplification multimer or label extender (e.g., at one or two sequences functioning to specifically associate the amplification oligomer with a label system). Where the second amplification system is an enzymatic amplification system, the sequences complimentary to components of a second amplification system typically act as a substrate for the enzymes or as a component of the substrate, e.g., in association with primer pairs in a PCR amplification.

Amplification oligomers can also provide a means to conserve information across process steps of a two-stage amplification. The amount of amplification oligomer from a first amplification can be correlated to an amount of the associated target nucleic acid present in the original sample. Amplification oligomer sequences complimentary to capture system sequences can be used in combination with other system components to physically sort them to predesignated locations on a second substrate unambiguously associated with a certain putative target nucleic acids. Amplification oligomer sequences complimentary to label system sequences can be used in combination with other system components to select predesignated label probes in a second amplification with a predesignated signal associated with a certain putative nucleic acid.

Capture Systems

The two-stage amplification systems of the invention can employ any number of different capture systems to capture nucleic acids of interest or capture amplification oligomers at solid supports in the first or second amplification stages, e.g., see the Capturing Nucleic Acids section, above. Capturing can be specific (e.g., through one or more specific hybridizations) or non-specific (e.g., through covalent chemistries or non-specific affinities). Capturing can be direct (e.g., through direct contact between the nucleic acid and the solid support capture moiety) or indirect (e.g., through intermediate associations).

In the simplest embodiment, capture systems are solid supports comprising chemical groups that interact directly and non-specifically with nucleic acids to be captured. For example, the capturing system can be nitrocellulose paper. Such capture systems are typically not preferred, e.g., in a first amplification of a complex sample because competition from nucleic acids not of interest and other sample components can reduce desired capture. Such capture systems are typically not preferred in many multiplexing embodiments of the two-stage amplification system, e.g., because amplification oligomers may not be directable to specific locations of such solid supports. However, direct non-specific capture solid supports can be useful, e.g., in capture of accumulated amplification oligomers after a wash step, e.g., for detection of a single nucleic acid of interest or where multiplexing is based on signaling from label systems having multiple signal sets.

In many two-stage amplification systems, the capture system comprises a solid support with little or no affinity for nucleic acids but with attached capture probes for direct or indirect capture of nucleic acids of interest or capture of amplification oligomers. Direct capture of target nucleic acids by capture probes, covalently attached to a solid support, has relatively simple kinetics and can provide a good signal with low background. Direct capture to capture probes avoids the need to engineer and manufacture linking capture extenders. However, direct capture of target nucleic acids with capture probes has the disadvantage of requiring a specially manufactured solid support for each target nucleic acid of interest.

Capture systems designed with a capture extender to link the target nucleic acid to the solid support through a generic capture probe offer the benefit that one solid support can be readily reconfigured for capture any number of different target nucleic acids by simply providing capture extenders with capture sequences complimentary to the intended target. Furthermore, a solid support with a generic capture probe can be configured to specifically capture two or more targets at once, possibly at different locations. Such solid supports can also be reusable to capture different targets in a second use. For example, in a first amplification, capture extenders with sequences complimentary to the generic capture probe and sequences complimentary to a target nucleic acid can indirectly capture the target at the solid support. Another solid support, e.g., with the same capture probe can capture amplification oligomers from the first amplification using a second capture extender having the sequence complimentary to the capture probe and having a sequence complimentary to the amplification oligomer. There is no need to specially manufacture two different solid supports for the first and second amplification stages. Systems designed to employ the generic capture probes avoid the need to specially manufacture different solid supports for different amplification assays directed to different nucleic acids of interest.

In multiplexed two-stage amplifications wherein deconvolution is based on the location of a signal, different amplification oligomers are typically captured at different locations in the capture system. The different locations can be, e.g., two or more microspheres, different positions along a conduit, different matrix positions on a planar solid support, different wells of a multi-well plate, and/or the like. Typically, solid supports at the different locations will have capture probes with different sequences at the different locations. In one embodiment, a solid support is provided with different capture probes at different locations so that different amplification oligomers accumulated in a first amplification can be captured directly for amplification and detection at those locations. In another embodiment, the a solid support is provided with different capture probes at different locations to capture capture extenders each combining a sequences specific to one capture probe and to one amplification oligomer, so that the amplification oligomers can be captured indirectly for amplification and detection at predesignated locations. In such a case, different sets of capture extenders could be used with a single generic matrixed solid support, e.g., to assay different classes of amplification oligomers (and associated nucleic acids of interest).

In another multiplexing embodiment, the solid supports comprise sets of beads with unique combinations of identification signals and capture probes. Such beads can be useful in capturing amplification oligomers in a second amplification similar to those described immediately above, but with deconvolution by correlating a label probe signal to a bead identification signal instead of a support matrix location. In another aspect of bead multiplexing, the beads have unique capture probes for sample nucleic acids of interest and the bead identification signal is used to particle sort the bead to a unique location for the second amplification and detection. Ultimately, a label signal at the unique location can be correlated to the presence of a particular nucleic acid of interest in the original sample.

Label Systems

Label systems of the present amplification systems are essentially as described above in the Methods section. Label systems in non-enzymatic two-stage amplifications function to provide a detectable signal in the presence of one or more captured amplification oligomers. Label systems include a sequence complimentary to an amplification oligomer sequence and two or more sequences complimentary to a label probe.

Label systems include at least an amplification multimer and label probes. Optionally, label systems include one or more label extenders, or the amplification multimer can be complimentary to and hybridize directly to the intended amplification oligomer. In a less preferred embodiment for most circumstances, the label system can simply be label probes. The amplification multimers can be as described above, e.g., a natural or unnatural nucleic acid comprising multiple sequences complimentary to label probe molecules, e.g., a branched DNA, a preamplifier strand associated with an amplifier strand, or a single un branched amplifier strand.

Typically, the label system sequence complimentary to the amplification oligomer is a sequence on a label extender or amplification multimer. In multiplexing embodiments wherein the presence of two or more different amplification oligomers is detected as two or more different signals, label systems with different signals are associated with each different amplification oligomer through unique complimentary sequences. For example, two-stage multiplexing amplification systems of the invention can include label systems in the second amplification stage with a first label extender complimentary to only a first amplification oligomer and to a first amplification multimer, which has multiple sequence sites complimentary to accumulate only those label probes having a first signal. The multiplexing amplification system can also have a second label extender complimentary only to a second amplification oligomer and to a second amplification multimer, which has multiple sequence sites complimentary to accumulate only those label probes having a second distinguishable signal. There can be third, fourth, and fifth signal sets of uniquely associating label extenders, amplification multimers and label probes, and so on. In this regard, a label system can include multiple uniquely associating sets with different distinguishable label signals to detect more than one amplification oligomer (and thereby, uniquely identify the presence of more than one nucleic acid of interest from a test sample).

In signal multiplexing embodiments, the label system can include two or more signal sets. The number of signal sets for signal multiplexing can range, e.g., from two to 1000, or more; typically from 4 to 20 sets, or about 10 sets. For example, in label systems using fluorescent labels, present detection technologies readily facilitate detection of several (e.g., 3 to 5) fluorescent probes at the same time. Larger numbers of signal sets can be distinguished, e.g., by detecting them separately in time sequence or at different locations. By using label probes with combinations of signals, the number of uniquely identifiable signal sets can be expanded. For example, label probes that each comprise two different labels can square the number of identifiable label probes for a given number of distinguishable signals.

Labels

Labels associated with label probes can provide the final highly amplified signal associated with the presence of a nucleic acid of interest in a sample. Moreover, labels can be provided with a range of distinguishable signals, e.g., useful in multiplexing schemes of the invention.

A wide variety of labels are well known in the art and can be adapted to the practice of the present inventions. For example, luminescent labels and light-scattering labels (e.g., colloidal gold particles) have been described. See, e.g., Csaki et al. (2002) "Gold nanoparticles as novel label for DNA diagnostics" Expert Rev Mol Diagn 2:187-93.

As another example, a number of fluorescent labels are well known in the art, including but not limited to, hydrophobic fluorophores (e.g., phycoerythrin, rhodamine, Alexa Fluor 488 and fluorescein), green fluorescent protein (GFP) and variants thereof (e.g., cyan fluorescent protein and yellow fluorescent protein), and quantum dots. See e.g., The Handbook: A Guide to Fluorescent Probes and Labeling Technologies, Tenth Edition or Web Edition (2006) from Invitrogen (available on the world wide web at probes.invitrogen.com/handbook), for descriptions of fluorophores emitting at various different wavelengths (including tandem conjugates of fluorophores that can facilitate simultaneous excitation and detection of multiple labeled species). For use of quantum dots as labels for biomolecules, see e.g., Dubertret et al. (2002) Science 298:1759; Nature Biotechnology (2003) 21:41-46; and Nature Biotechnology (2003) 21:47-51.

Labels can be introduced to molecules, e.g. polynucleotides, during synthesis or by post-synthetic reactions by techniques established in the art; for example, kits for fluorescently labeling polynucleotides with various fluorophores are available from Molecular Probes, Inc. ((www.) molecularprobes.com), and fluorophore-containing phosphoramidites for use in nucleic acid synthesis are commercially available. Similarly, signals from the labels (e.g., absorption by and/or fluorescent emission from a fluorescent label) can be detected by essentially any method known in the art. For example, multicolor detection, detection of FRET, fluorescence polarization, and the like, are well known in the art.

Multiplexing Systems

Multiplexing systems can include, e.g., deconvolution by location of signals from a second amplification, by detection of different second amplification signals at the same location, by detection of three or more second amplification signals at two locations, or by detection of a second amplification signal from beads sorted after a first amplification, as discussed above.

Figure 5A:
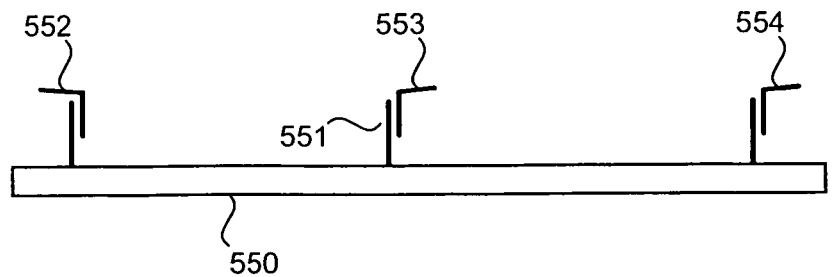
Figure 5B:
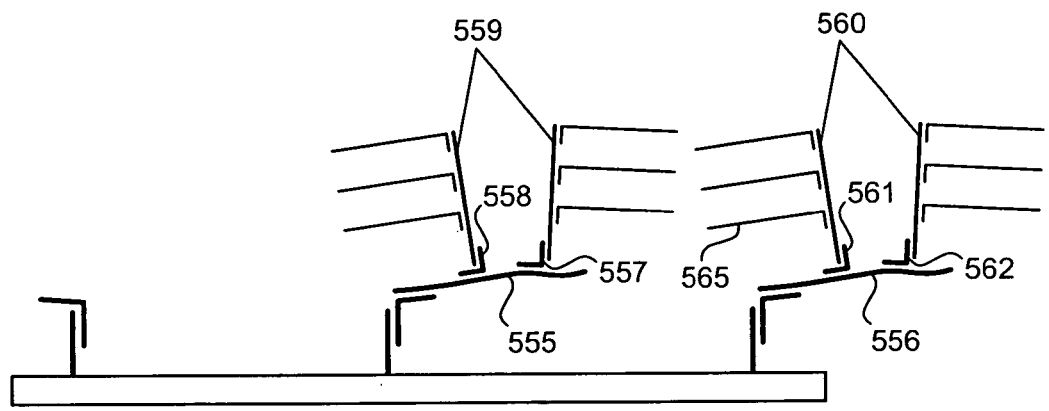
Figure 5C:
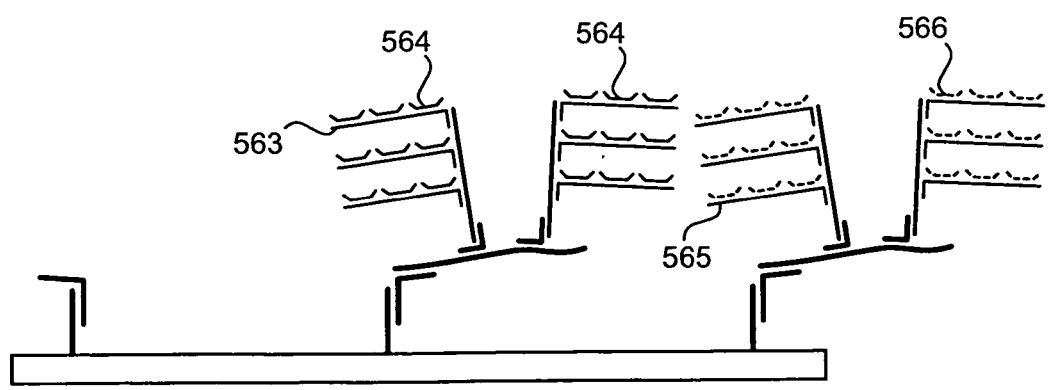

An exemplary embodiment of a two-stage amplification with multiplexing and deconvolution by bead identity is schematically illustrated in FIG. 5. In FIGS. 5A to 5C, a first amplification provides an accumulation of two different amplification oligomers associated with the presence of two different target nucleic acids of interest. FIGS. 5D to 5G describe a second amplification on beads wherein the accumulated amplification oligomers of the first amplification function as substrate on different beads. Deconvolution of signals to identify nucleic acids of interest in the sample can be by correlation of amplification label probe signals to associated bead identification signals.

FIG. 5A shows solid support 550 with first capture probes 551 having captures three different first capture extenders 552, 553 and 554. The three first capture extenders have the same capture probe complimentary sequences, but C-3 sequences complimentary to different sample nucleic acids of interest. As shown in FIG. 5B, different nucleic acids of interest 555 and 556 are captured from a test sample, but the nucleic acid complimentary to capture extender 552 was not present in the sample. First label extenders 557 and 558 are complimentary to nucleic acid of interest 555 but not to 556, and complimentary to preamplifiers 559 but not to preamplifiers 560. First label extenders 561 and 562 are complimentary to nucleic acid of interest 556 but not to 555, and complimentary to preamplifiers 560 but not to preamplifiers 559. As shown in FIG. 5C, preamplifiers 559 specifically hybridize to amplifiers 563 and to amplification oligomers 564 but not amplifiers 565 or amplification oligomers 566. With the first amplification configured in this way: 1) no amplification oligomers are accumulated in association with the nucleic acid of interest (not present in the sample) complimentary to capture extender 552, 2) amplification oligomers 564 are accumulated in association with nucleic acid of interest 555, and 3) amplification oligomers 566 are accumulated in association with nucleic acid of interest 556 at the solid support 550.

For the second amplification, FIG. 5D illustrates three distinguishable subsets of microspheres 501, 502, and 503, which have associated therewith second capture probes 504, 505, and 506, respectively. Each capture probe includes a sequence C-2 (530), which is different from subset to subset of microspheres. The three subsets of microspheres are combined to form pooled population 508, as shown in FIG. 5E. A subset of capture extenders is provided for each nucleic acid of interest; subset 511 for amplification oligomer 564, subset 512 for amplification oligomer 567 which is not present, and subset 513 for amplification oligomer 566. Each capture extender includes sequences C-1 (531, complementary to the respective capture probe's sequence C-2) and C-3 (532, complementary to a sequence in the corresponding amplification oligomer). Three subsets of label extenders (521, 522, and 523 for amplification oligomers 564, 567, and 566, respectively) and three subsets of blocking probes (524, 525, and 526 for amplification oligomers 564, 567, and 566, respectively) are also optionally provided. Optionally, the system can employ a single set of label extenders complimentary to the same sequence on all amplification oligomers. Each label extender includes sequences L-1 (534, complementary to an amplification oligomer sequence) and L-2 (535, e.g., complementary to amplification multimer M-1 sequences).

Subsets of label extenders 521 and 523 are hybridized to amplification oligomers 564 and 566, respectively. In addition, amplification oligomers 564 and 566 are hybridized to their corresponding subset of capture extenders (511 and 513, respectively), and the capture extenders are hybridized to the corresponding capture probes (504 and 506, respectively), capturing nucleic acids 564 and 566 on microspheres 501 and 503, respectively, as shown in FIG. 5F. Materials not bound to the microspheres (e.g., capture extenders 512, label extenders 522, and blocking probes 525, etc.) are separated from the microspheres by washing. Label probe system 540 including amplification multimer 541 (which includes sequences M-1 537 and M-2 538), and label probes 542 (which contain label 543) is provided. Label extenders 521 and 523 are hybridized to amplification multimers 541, and label probes 542 are hybridized to the amplification multimers, as shown in FIG. 5G. Materials not captured on the microspheres are optionally removed by washing the microspheres. Microspheres from each subset are identified, e.g., by their fluorescent emission spectrum (i.e., ratio and intensity of $\lambda_2$ and $\lambda_3$, FIG. 6), and the presence or absence of the label on each subset of microspheres is detected ($\lambda_1$, FIG. 6). Since each nucleic acid of interest is associated with particular amplification oligomers and a distinct subset of microspheres, the presence of the label on a given subset of microspheres correlates with the presence of the corresponding nucleic acid in the original sample.

In optional systems, the microspheres described immediately above could be replaced with matrix locations on a planar solid support. Like the microsphere subsets, each location could have a different capture probe. The accumulated amplification oligomers of the first amplification could be melted into a solution and transferred to contact the solid support locations. After contact with the labeling system and washing, the presence of one or two or more nucleic acids of interest in the sample could be determined as the presence of a label probe signal at a predetermined location on the solid support.

The methods are useful for multiplexed detection of nucleic acids, optionally highly multiplexed detection. Thus, the two or more nucleic acids of interest (i.e., the nucleic acids to be detected) optionally comprise five or more, 10 or more, 20 or more, 30 or more, 40 or more, 50 or more, or even 100 or more nucleic acids of interest, while the two or more subsets of m first capture extenders, solid support locations, second capture extenders or label extenders can comprise five or more, 10 or more, 20 or more, 30 or more, 40 or more, 50 or more, or even 100 or more subsets.

Solid Support Capture Arrays

An array of capture probes can be prepared on a solid support (e.g., a membrane, a glass or plastic slide, a silicon or quartz chip, a plate, or other spatially addressable solid support), typically with each capture probe bound (e.g., electrostatically or covalently bound, directly or via a linker) to the support at a unique selected location. Methods of making, using, and analyzing such arrays (e.g., microarrays) are well known in the art. See, e.g., Baldi et al. (2002) DNA Microarrays and Gene Expression: From Experiments to Data Analysis and Modeling, Cambridge University Press; Beaucage (2001) "Strategies in the preparation of DNA oligonucleotide arrays for diagnostic applications" Curr Med Chem 8:1213-1244; Schena, ed. (2000) Microarray Biochip Technology, pp. 19-38, Eaton Publishing; technical note "Agilent SurePrint Technology: Content centered microarray design enabling speed and flexibility" available on the web at chem.agilent.com/temp/rad01539/00039489.pdf; and references therein. Arrays of pre-synthesized polynucleotides can be formed (e.g., printed), for example, using commercially available instruments such as a GMS 417 Arrayer (Affymetrix, Santa Clara, Calif.). Alternatively, the polynucleotides can be synthesized at the selected positions on the solid support; see, e.g., U.S. Pat. Nos. 6,852,490 and 6,306,643, each to Gentanlen and Chee entitled "Methods of using an array of pooled probes in genetic analysis."

Suitable solid supports are commercially readily available. For example, a variety of membranes (e.g., nylon, PVDF, and nitrocellulose membranes) are commercially available, e.g., from Sigma-Aldrich, Inc. ((www.) sigmaaldrich.com). As another example, surface-modified and pre-coated slides with a variety of surface chemistries are commercially available, e.g., from TeleChem International ((www.) arrayit.com), Corning, Inc. (Corning, N.Y.), or Greiner Bio-One, Inc. ((www.) greinerbiooneinc.com). For example, silanated and silyated slides with free amino and aldehyde groups, respectively, are available and permit covalent coupling of molecules (e.g., polynucleotides with free aldehyde, amine, or other reactive groups) to the slides. As another example, slides with surface streptavidin are available and can bind biotinylated capture probes. In addition, services that produce arrays of polynucleotides of the customer's choice are commercially available, e.g., from TeleChem International ((www.) arrayit.com) and Agilent Technologies (Palo Alto, Calif.).

Suitable instruments, software, and the like for analyzing arrays to distinguish selected positions on the solid support and to detect the presence or absence of a label (e.g., a fluorescently labeled label probe) at each position are commercially available. For example, microarray readers are available, e.g., from Agilent Technologies (Palo Alto, Calif.), Affymetrix (Santa Clara, Calif.), and Zeptosens (Switzerland).

Label Probe Detectors

Label probe products of the second amplification can be detected using any hardware appropriate to the chosen solid support and label. Where the second amplification takes place on a nitrocellulose membrane and the label is an enzyme, the detector can simply be, e.g., a technician visually inspecting the membrane for development of a chromogen. Where the solid support is a floor of a well in a multiwell plate and the label is a chemiluminescent enzyme, a sequential or parallel formatted plate reader can be appropriate. In embodiments wherein the solid support is a bead with an identification signal, the label signal is typically detected using a Fluorometer associated with a flow cytometer or with a charge coupled device viewing the beads settled into a two dimensional array. These exemplary embodiments of appropriate detectors are not limiting and one skilled in the art would appreciate appropriate variations.

Kits

Yet another general class of embodiments provides a kit for detecting one or more nucleic acids of interest. In one aspect, the kit includes a first solid support, a first amplification multimer, and one or more amplification oligomers. For kits providing a non-enzymatic second amplification, the kit can further include a second solid support, and a label system. In certain embodiments, the kit can include appropriate capture extenders, blocking probes, and/or label extenders. The solid supports can comprise, e.g., multiwell plates, planar surfaces, planar surfaces with matrixed arrays, and/or particles. Capture specificity of solid support locations can be by, e.g., well position, matrix location or bead identity signal.

In multiplexed embodiments of kits, many components can be represented with two or more different subsets. For example, the solid support particles can include a population comprising two or more subsets of particles, with a plurality of the particles in each subset being distinguishable from a plurality of the particles in every other subset. The particles in each subset can have a different set of capture probe bonded to the surface. In another aspect, the kit includes a solid support comprising two or more capture probes, wherein each capture probe is provided at a selected position on the solid support.

Example

Zip Codes for Multiplexed Assays

The following examples are offered to illustrate, but not to limit the claimed invention.

The following prophetic example of a multiplexed two-step amplification showing how a first amplification can amplify specific amplification oligomers with unique zip code sequences to generate a highly amplified and deconvolutable signal in a second amplification.

In a first parallel amplification (shown in FIG. 7), different target nucleic acids of interest 70 (gene 1), 80 (gene 2) and 90 (gene 3), are captured on capture probes 71, 81 and 91. The target nucleic acids specifically hybridize to amplification multimers 72, 82, and 92. The amplification multimers each specifically hybridize with up to 15 amplification oligomers (for purposes of clarity in the figure, only one is shown per multimer) 73, 83, and 93; thereby amplifying each single target nucleic acid to 15 amplification oligomers in the first amplification.

The amplification oligomers each comprise a 28 base pair compliment (74, 84, 94) to a second amplification preamplifier, a 25 to 60 base pair compliment (75, 85, 95) to the replicate amplification multimer sequences of the first amplification, and a 50 base pair zip code sequence (76, 86, 96) complimentary to the capture sequences of the second amplification. In the present example, the amplification multimer compliment of each different amplification oligomer is not complimentary to the corresponding sequence on the other amplification oligomers. In this way, the presence of each different target nucleic acid in the first amplification can result in a specific signal in the second amplification. That is, in this example the amplification multimer compliment and capture probe compliment (zip code) can function together to provide an amplified signal at a particular substrate location, e.g., a bead surface.

Figure 7:
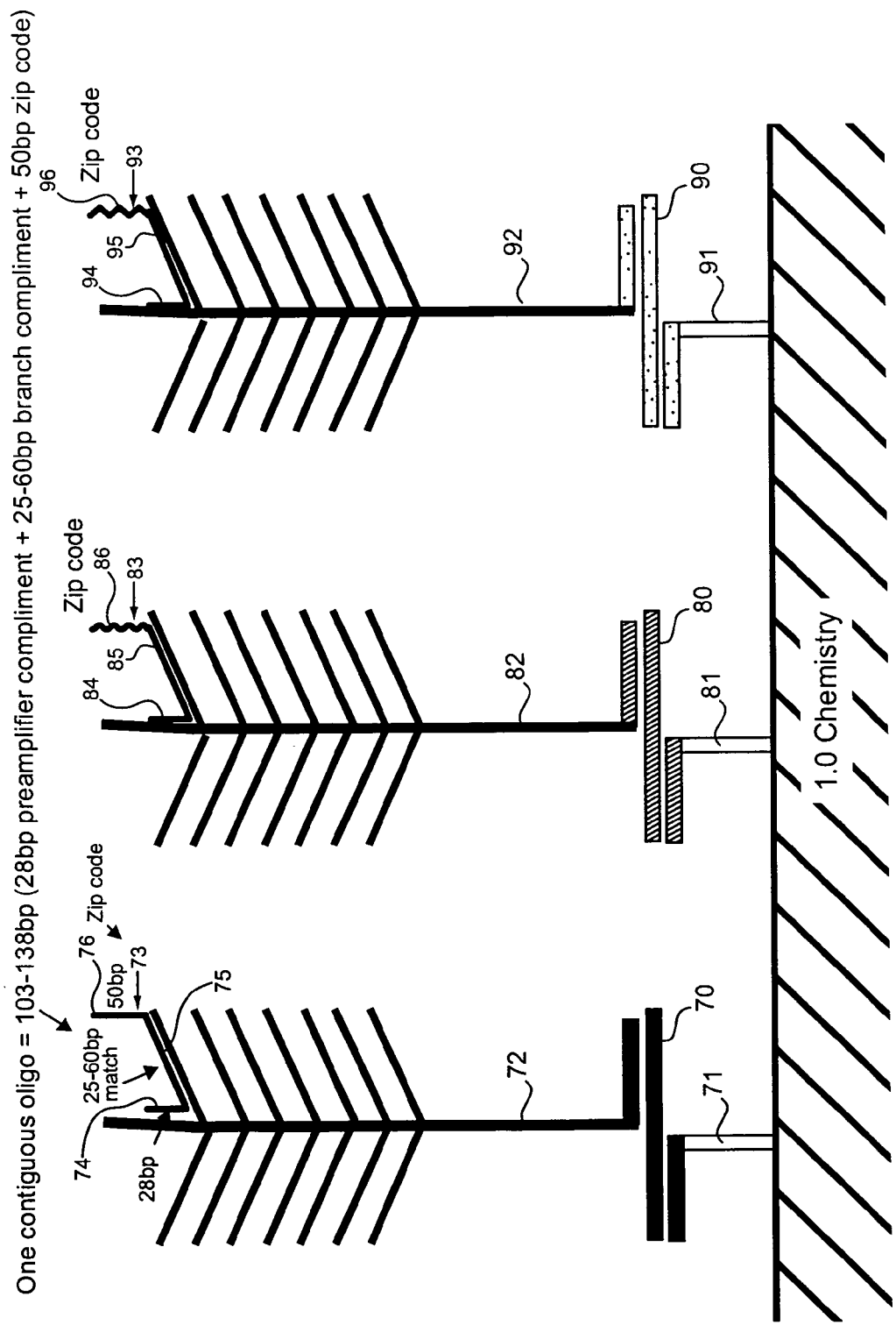
FIG. 7 is a schematic diagram showing an exemplary embodiment of a two-step multiplexed amplification. A variety of amplification oligomers with different zip codes (e.g., compliments to second amplification C-3 sequences) are enriched in a first amplification wherein each amplification multimer has 15 replicate sequences complimentary to accumulate amplification oligomer sequences.
Figure 8:
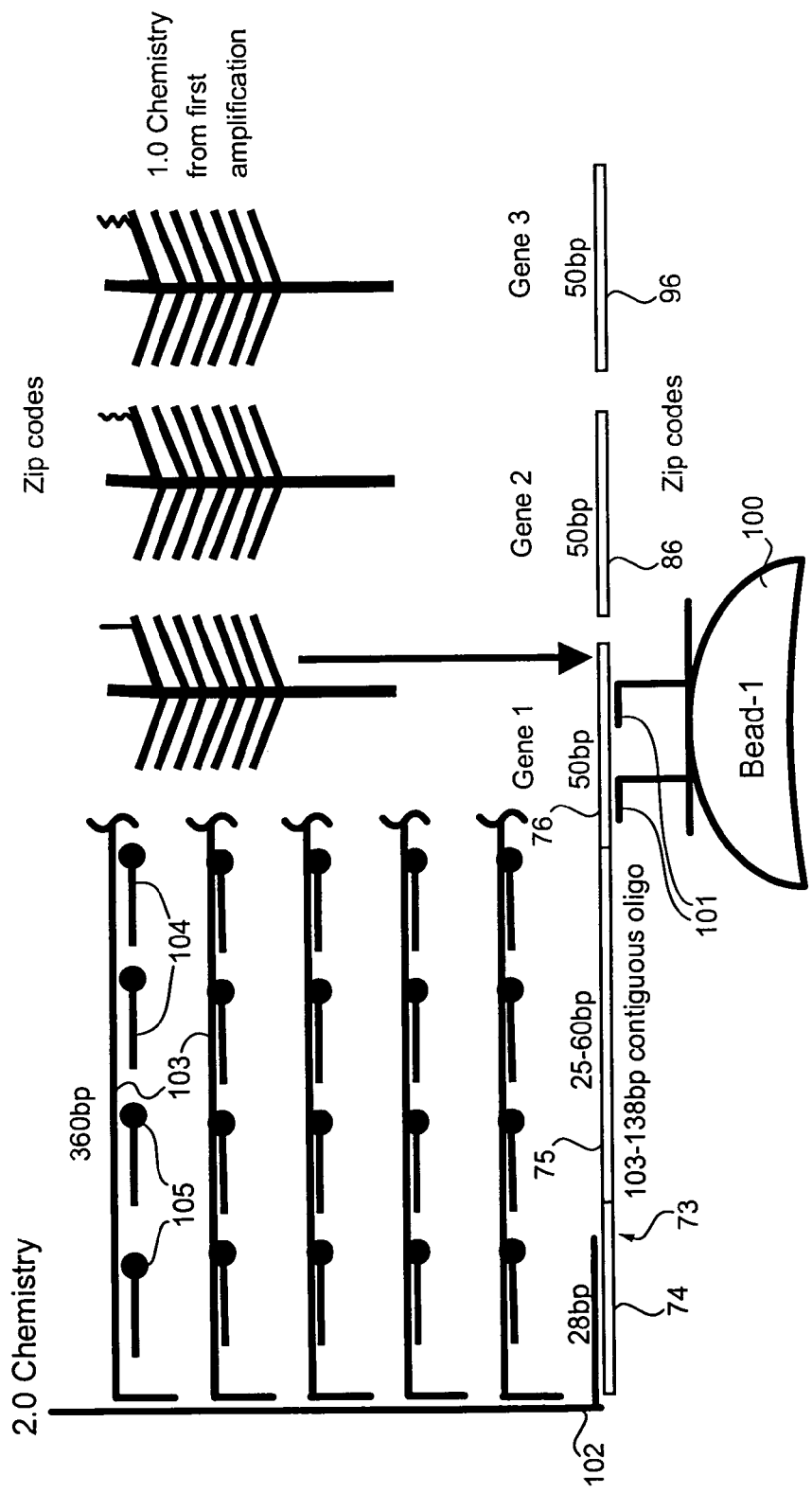
FIG. 8 is a schematic diagram showing a second amplification step wherein the variety of amplification oligomers accumulated in the first amplification (e.g., of FIG. 7) are each amplified 400-fold on amplification multimers of specific beads in a second amplification.

After the amplification of FIG. 7 is washed and melted, the amplification oligomer product of the first amplification is transferred to a second amplification system, as shown in FIG. 8. The second amplification has beads 100 (only the bead associated with the first gene is shown here for clarity) each having unique capture probe sequences 101 (only one set shown here for clarity) specifically complimentary to only one of the zip code sequences of the amplification oligomer assemblage. In this way, the zip code sequence of the amplification oligomer can function to allow capture only at a particular identifiable bead surface. For example, the amplification oligomer 73 associated with the gene 1 target can be uniquely captured at the zip code sequence 76 by a capture sequence on bead 100 having a unique identifier signal. The preamplifier compliment can hybridize to a generic preamplifier 102 which in turn hybridizes to 5 generic linear amplifiers 103. Each linear amplifier 103 can hybridize to about 20 label probes 104 (for clarity, not all the amplifier length and label probes are shown), thus for every amplification oligomer in the second amplification a signal can be produced from about 400 labels 105 on the bead 100.

Similar second amplifications can take place on other beads, e.g., in the same solution, with capture sequences specific to zip code compliments on the other amplification oligomer products of the first amplification. The beads can have different identification signals so that generic label signals on specifically identified beads can unambiguously identify the presence of associated target genes in the first amplification.

In the two-step amplification of this example, the 15-fold amplification of target to amplification oligomer and the 400-fold amplification of the second amplification of amplification oligomer to label probe result in an overall 6000-fold amplification from target to label probe. Moreover, the specific sequence function of the amplification oligomers (unique specific amplification multimer compliments and zip codes) allow deconvolution of detected signals, so that the presence and/or quantity of two or more targets can be measured at the same time from the same sample.

It is understood that the examples and embodiments described herein are for illustrative purposes only and that various modifications or changes in light thereof will be suggested to persons skilled in the art and are to be included within the spirit and purview of this application and scope of the appended claims.

While the foregoing invention has been described in some detail for purposes of clarity and understanding, it will be clear to one skilled in the art from a reading of this disclosure that various changes in form and detail can be made without departing from the true scope of the invention. For example, many of the methods, compositions and apparatus described above can be used in various combinations.

All publications, patents, patent applications, and/or other documents cited in this application are incorporated by reference in their entirety for all purposes to the same extent as if each individual publication, patent, patent application, and/or other document were individually indicated to be incorporated by reference for all purposes.

What is claimed is:

1. An amplification oligomer comprising:
    a first a nucleotide sequence complementary to an amplification multimer repeat sequence of a first amplification multimer; and,
    a second nucleotide sequence, wherein the second nucleotide sequence is complementary to (i) a second amplification multimer sequence of a second amplification multimer or (ii) a label extender sequence of a label extender,
    wherein the label extender comprises an additional sequence complementary to the second amplification multimer sequence, and
    wherein the amplification oligomer is a single-stranded nucleic acid.

2. The amplification oligomer of claim 1, further comprising a third nucleotide sequence complementary to a capture extender sequence or complementary to a capture probe sequence.

3. The amplification oligomer of claim 2, wherein the third nucleotide sequence comprises from 20 to 60 nucleotides.

4. The amplification oligomer of claim 1, wherein the first amplification multimer is a component of a first bDNA assay, and the second amplification multimer is a component of a second bDNA assay.

5. The amplification oligomer of claim 1, wherein the second nucleotide sequence comprises from 30 to 60 nucleotides.

6. The amplification oligomer of claim 1, wherein the second nucleotide sequence comprises from 20 to 40 nucleotides.

7. The amplification oligomer of claim 1, wherein the amplification oligomer is from 100 to 150 nucleotides in length.

8. The amplification oligomer of claim 1, wherein the second nucleotide sequence hybridizes to the second amplification multimer through a label extender.

9. The amplification oligomer of claim 2, wherein the capture extender or the capture probe is bound to a particle comprising an identification signal.

10. Two or more of the amplification oligomers of claim 2, wherein:
   a) a first amplification oligomer comprises a nucleotide sequence complementary to the third sequence different from a capture extender target capture sequence complement of a second amplification oligomer or
   b) the first amplification oligomer comprises a third nucleotide sequence complementary to a capture probe target capture sequence different from a capture probe target capture sequence of the second amplification oligomer.

11. The amplification oligomer of claim 2, wherein the complementary sequences are in the following order:
   1) the first nucleotide sequence;
   2) the third nucleotide sequence
   3) the second nucleotide sequence.

12. The amplification oligomer of claim 2, further comprising two or more third nucleotide sequences, thereby providing for cooperative hybridization.

13. The amplification oligomer of claim 1, further comprising two or more of the second nucleotide sequences.

14. The amplification oligomer of claim 2, wherein the first nucleotide sequence is between:
   the third nucleotide sequence, and
   the second nucleotide.

15. A method of identifying one or more amplification oligomers of claim 1, the method comprising:
   providing a first label system comprising a first sequence complementary to a first label probe comprising a first label;
   providing a sample comprising or suspected of comprising a first amplification oligomer comprising a sequence complementary to a component of the first label system;
   hybridizing the sample with the first label system; and,
   detecting a signal from the first label;
   wherein detection of the signal from the first label indicates the presence of the first amplification oligomer in the sample.

16. The method of claim 15, wherein the first system comprises:
   a) a label probe comprising a sequence complementary to an amplification multimer, which amplification multimer comprises a sequence complementary to a label extender, which label extender comprises a sequence complementary to the first amplification oligomer, or
   b) a label probe comprising a sequence complementary to an amplification multimer, which amplification multimer comprises a sequence complementary to the amplification oligomer.

17. The method of claim 15, wherein the label system comprises a label extender functioning to hybridize the first amplification oligomer to the first label system.

18. The method of claim 15, further comprising providing a second label system comprising a second sequence complementary to a second label probe comprising a second label different from the first label;
   providing the sample comprising or suspected of comprising a second amplification oligomer comprising a sequence complementary to a component of the second label system;
   hybridizing the sample with the first and second label system; and,
   detecting a signal from the first label or from the second label;
   wherein detection of the signal from the first label indicates the presence of the first amplification oligomer in the sample or detection of the signal from the second label indicates the presence of the second amplification oligomer in the sample.

19. The method of claim 18, wherein the first and second detectable markers comprise the same type of label but with different signals, or wherein the first and second detectable markers comprise different types of labels.

20. The method of claim 18, further comprising identifying the first and second amplification oligomers at substantially the same location by detecting both the first and second labels at the location.

21. The method of claim 18, further comprising identifying the two or more amplification oligomers at the same time by detecting both the first and second labels at substantially the same time.

22. An amplification oligomer comprising:
   a first nucleotide sequence adapted to be complementary to an amplification multimer repeat sequence of a first amplification multimer; and,
   a second nucleotide sequence adapted to be complementary to a target complement sequence of a label extender or to a target complement of a second amplification multimer;
   wherein the first nucleotide sequence is adapted to hybridize with its complement with Tm within about 5° C. of the Tm for hybridization of the second nucleotide sequence with its respective complement; and
   wherein the amplification oligomer is a single-stranded nucleic acid.

23. The amplification oligomer of claim 22, wherein the amplification oligomer does not include a complement to a capture system.

24. Two or more amplification oligomers of claim 22, wherein the two or more amplification oligomers comprise:
   different amplification multimer repeat sequence complements;
   comprise different second amplification multimer target sequence complements;
   or comprise different label extender target complements.

25. The amplification oligomer of claim 22, wherein the amplification oligomer is other than a labeled probe.

26. The amplification oligomer of claim 1, wherein the amplification oligomer is not in a complex with a first and second amplification multimer.

27. The amplification oligomer of claim 1, wherein the amplification oligomer is adapted to function as a target nucleic acid of interest for the second amplification multimer.

28. The amplification oligomer of claim 1, wherein the first amplification multimer is different from the second amplification multimer.

29. An amplification oligomer comprising:
   a nucleotide sequence complementary to an amplification multimer repeat sequence of a first amplification multimer; and,
   a nucleotide sequence complementary to an amplification multimer polynucleotide sequence adapted to hybridize to a target sequence of a second amplification multimer different from the first amplification multimer;

wherein the amplification oligomer is adapted to function as a target nucleic acid of interest for the second amplification multimer.

30. An amplification oligomer comprising:

a first nucleotide sequence complementary to an amplification multimer repeat sequence of a first amplification multimer; and, a second nucleotide sequence complementary to (i) a second amplification multimer sequence of a second amplification multimer or (ii) a label extender sequence of a label extender, wherein the label extender comprises an additional sequence complementary to the second amplification multimer sequence, and wherein the amplification oligomer is adapted to function as a target nucleic acid of interest for the second amplification multimer.

* * * * *